United States Patent
Dugar et al.

(10) Patent No.: US 10,207,993 B2
(45) Date of Patent: Feb. 19, 2019

(54) COMPOUNDS AS ANTI-TUBERCULAR AGENTS

(71) Applicants: SPHAERA PHARMA PVT. LTD., Gurgaon, Haryana (IN); DRUG DISCOVERY RESEARCH CENTRE, Gurgaon, Haryana (IN)

(72) Inventors: Sundeep Dugar, Haryana (IN); Dinesh Mahajan, Haryana (IN); Santosh Kumar Rai, Haryana (IN); Kanury Rao, Haryana (IN); Varshneya Singh, Haryana (IN)

(73) Assignees: SPHAERA PHARMA PVT. LTD., Gurgaon, Haryana (IN); DRUG DISCOVERY RESEARCH CENTRE, Gurgaon, Haryana (IN)

( * ) Notice: Subject to any disclaimer, the term of this patent is extended or adjusted under 35 U.S.C. 154(b) by 0 days.

(21) Appl. No.: 15/674,033

(22) Filed: Aug. 10, 2017

(65) Prior Publication Data
US 2017/0334851 A1    Nov. 23, 2017

Related U.S. Application Data

(62) Division of application No. 15/313,986, filed as application No. PCT/IN2015/000226 on Jun. 1, 2015.

(30) Foreign Application Priority Data

May 30, 2014   (IN) .......................... 1431/DEL/2014

(51) Int. Cl.
| | | |
|---|---|---|
| A61K 45/06 | (2006.01) |
| A61K 31/445 | (2006.01) |
| C07D 205/04 | (2006.01) |
| C07D 207/09 | (2006.01) |
| C07D 207/12 | (2006.01) |
| C07D 211/42 | (2006.01) |
| C07D 211/46 | (2006.01) |
| C07D 211/56 | (2006.01) |
| C07D 211/58 | (2006.01) |
| C07D 213/75 | (2006.01) |
| C07D 265/30 | (2006.01) |
| C07D 453/04 | (2006.01) |
| C07C 59/64 | (2006.01) |

(52) U.S. Cl.
CPC .......... *C07D 211/42* (2013.01); *A61K 31/445* (2013.01); *A61K 45/06* (2013.01); *C07C 59/64* (2013.01); *C07D 205/04* (2013.01); *C07D 207/09* (2013.01); *C07D 207/12* (2013.01); *C07D 211/46* (2013.01); *C07D 211/56* (2013.01); *C07D 211/58* (2013.01); *C07D 213/75* (2013.01); *C07D 265/30* (2013.01); *C07D 453/04* (2013.01)

(58) Field of Classification Search
None
See application file for complete search history.

(56) References Cited

U.S. PATENT DOCUMENTS

| | | |
|---|---|---|
| 2,844,591 A | 7/1958 | Feldkamp et al. |
| 2,918,408 A | 12/1959 | Biel |
| 2,955,114 A | 10/1960 | Biel |
| 2,995,492 A | 8/1961 | Biel |
| 6,482,837 B1 | 11/2002 | Wood |

FOREIGN PATENT DOCUMENTS

| | | |
|---|---|---|
| AU | 7102701 | 1/2002 |
| CA | 2218479 | 10/1996 |
| CA | 2155320 | 8/2013 |
| EP | 0 751 127 | 1/1997 |
| EP | 0 913 393 | 5/1999 |
| WO | WO-98/50022 | 11/1998 |

OTHER PUBLICATIONS

RN 1157986-55-4 (Entered STN: Jun. 15, 2009), CAS Registry (Online) STN International, Columbus, Ohio, US.
RN 1271712-15-2 (Entered STN: Mar. 29, 2011), CAS Registry (Online) STN International, Columbus, Ohio, US.
RN 57258-61-4 (Entered STN: Nov. 16, 1984), CAS Registry (Online) STN International, Columbus, Ohio, US.
RN 7021-09-2(Entered STN: Nov. 16, 1984), CAS Registry (Online) STN International, Columbus, Ohio, US.
International Search Report issued in International Patent Application No. PCT/IN2015/000226 dated Dec. 15, 2015.
U.S. Office Action issued in U.S. Appl. No. 15/313,986, dated Aug. 17, 2017.

*Primary Examiner* — Zinna Northington Davis
(74) *Attorney, Agent, or Firm* — Foley & Lardner LLP

(57) ABSTRACT

The present invention relates to novel compounds of formula (1):

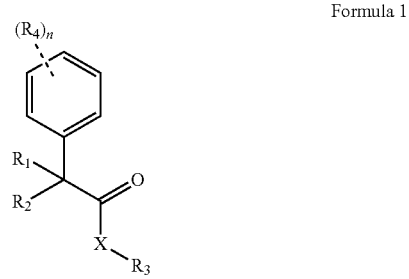

Formula 1

The present invention also discloses compounds of formula (1) along with other pharmaceutical acceptable excipients and use of the compounds as anti-tubercular agents.

9 Claims, 10 Drawing Sheets

Untreated
(Co localization coefficient 0.196 ± 0.057)

+ 1085
(Co localization coefficient 0.315 ± 0.048)

Untreated
(Co localization coefficient 0.232 ± 0.064)

+ 1085
(Co localization coefficient 0.435 ± 0.085)

COMPOUNDS AS ANTI-TUBERCULAR AGENTS

CROSS-REFERENCE TO RELATED APPLICATIONS

The present application is a divisional of U.S. application Ser. No. 15/313,986, filed Nov. 25, 2016, which is a U.S. national stage application of International Patent Application No. PCT/IN2015/000226, filed on Jun. 1, 2015, which claims the benefit of priority to Indian Patent Application No. 1431/DEL/2014, filed on May 30, 2014, the entire contents of which are hereby incorporated by reference.

FIELD OF THE INVENTION

The present invention relates to novel compounds useful as anti-tubercular agents. More particularly, the present invention relates to substituted derivatives, methods for their preparation, pharmaceutical compositions containing these compounds and uses of these compounds in the treatment of tuberculosis.

BACKGROUND OF THE INVENTION

Tuberculosis causes nearly two million deaths annually. Recent years have witnessed a resurgence of efforts directed at tuberculosis (TB) drug research and development. An analysis of the chronology of anti-tuberculosis therapy suggests a renewed interest in tuberculosis research. Since the 1960s and 70s same generation of antibiotics or their derivatives are being used against *Mycobacterium tuberculosis* even though there is resistance against the drugs with the development of drug resistant strains such as Multidrug resistance TB (MDR-TB) which are resistant to at least isoniazid (INH) and rifampicin (RMP), the two most powerful first-line treatment anti-TB drugs; extensively drug resistance TB (XDR-TB) which are resistant to isoniazid and rifampin, plus any fluoroquinolone and at least one of three injectable second-line drugs such as amikacin, kanamycin, or capreomycin and totally drug resistance TB (TDR-TB) which are resistant to all first and second line drugs tested such as isoniazid, rifampicin, streptomycin, ethambutol, pyrazinamide, ethionamide, para-aminosalicylic acid, cycloserine, ofloxacin, amikacin, ciprofloxacin, capreomycin, kanamycin.

India has the world's one of the highest burden of tuberculosis, wherein MDR tuberculosis accounts for nearly 5 lakhs cases annually which have been increased by more than 6% in the past 10 years.

It is said that *M. tuberculosis* develops resistance to drugs by induced or spontaneous mutation of its genome. It is also hypothesized that in case of certain drugs the bacterial cell wall, does not permit adequate permeability, thereby resulting in inadequate/minor amount of drug entering the bacteria. Such amount is insufficient to kill the bacteria, but the presence of minor amount, induces the bacteria to become resistant to the same. It is also hypothesized that *M. tuberculosis* acquires resistance by modification of its enzyme by unknown mechanisms. Traditional antitubercular drugs administered via oral route, act by inhibiting the synthesis of mycolic acid and/or by inhibiting the mycobacterial arabinosyltransferase, an essential component of mycobacterial cell wall. Few systemic antitubercular drugs also act by crossing the lipid bilayer and bind to one of the ribosome sub-unit, inhibiting the protein synthesis. Based on mechanism of action of these drugs, these drugs have a high probability of inducing mutation and/or have problems of permeability, increasing the chances of drug resistant strains.

G-protein coupled receptors such as GPR109A also plays an important role in tuberculosis. GPR109A receptor is located on the cell surface and inhibits adenylyl cyclase along with consequent suppression of PKA-signaling resulting in reduced triglyceride turnover which is further responsible for accumulation of lipid body inside the cell. Increase in the concentration of lipid body inside the cell favors the growth of *M. tuberculosis* and prevents respiratory burst. A GPR109A inhibitor prevents the formation of lipid body by creating a hostile environment for the tuberculosis and thus induces respiratory burst. Host macrophages infected by *M. tuberculosis* acquire foamy phenotype characterized by the intracellular accumulation of lipid bodies induced by pathogen through modulation of lipolysis of neutral lipids. This dysregulation influences the lipolysis by modulating the cAMP dependent signaling pathway.

Current resistant tuberculosis treatment, has greater risk of side effects and lasts for 18-24 months and target processes or enzymes within *M. tuberculosis* but suffers from the risk of generating newer variants exhibiting drug resistance. Since, *M. tuberculosis* survives within the human macrophage through modulation of a range of host cellular processes hence, a pharmacological target within the host that has been co-opted by *M. tuberculosis* for its survival should be a breakthrough approach for therapy. Additionally such an approach should be insensitive to whether the infecting strain was drug sensitive or drug resistant and preclude the development of resistance.

OBJECT OF THE INVENTION

An object of the invention is to provide compounds useful as anti-tubercular agents.

SUMMARY OF THE INVENTION

The present invention provides novel compounds of Formula 1:

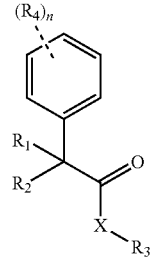

Formula 1 wherein,

X is selected from O, NH or N(alkyl);

$R_1$ and $R_2$ are independently selected from hydrogen, deuterium, hydroxyl, $C_{1-10}$ straight chain or branched chain alkyl, 3-7 membered cycloalkyl, $C_{1-6}$alkoxy, aryl, amino, NH(alkyl), N(alkyl)$_2$, OCOR$_5$, heteroaryl containing 1-3 heteroatoms selected from the group comprising O, N or S; or $R_1$ and $R_2$ may combined to form an aryl or a heteroaryl ring containing 1-3 heteroatoms selected from the group comprising O, N or S;

$R_3$ is selected from hydrogen, hydroxyl, $C_{1-6}$ straight chain or branched chain alkyl, 3-7 membered cycloalkyl, C$_{1-6}$alkoxy, aryl, aromatic or non-aromatic heterocyclic ring or fused heterocyclic rings elected from:

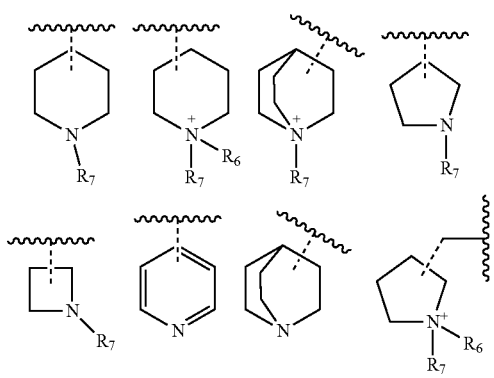

X may in conjunction with R3 form a 5-7 membered heterocyclic ring comprising 1-3 heteroatoms selected from group comprising N, O or S. The heterocyclic ring be further substituted with one or more lower alkyl groups, halogens, amino, NH(alkyl), N(alkyl)2, NH-aralkyl;

R4 is selected from a hydrogen, lower straight chain or branched alkyl, halogen, deuterium, C1-6 alkoxy, amino, NH(alkyl), N(alkyl)2, —COOR8, CONR8R9;

R5 is hydrogen, hydroxy, C1-6alkyl, C1-6alkoxy, amino, NH(alkyl), N(alkyl)2;

R6 and R7 are independently selected from the group comprising hydrogen, C1-10 alkyl, —COR8, —CH2OCOR8, —CH2OCONHR8R9, —COOR8, —CONR8R9, —SO2R8, aryl, aralkyl;

R8 and R9 are independently selected from the group comprising hydrogen, or C1-6 straight chain or branched chain alkyl;

n is 1, 2, or 3. and salts, hydrates and stereoisomers thereof.

DETAILED DESCRIPTION OF THE INVENTION

A. Compounds of the Present Invention

Figure 1:
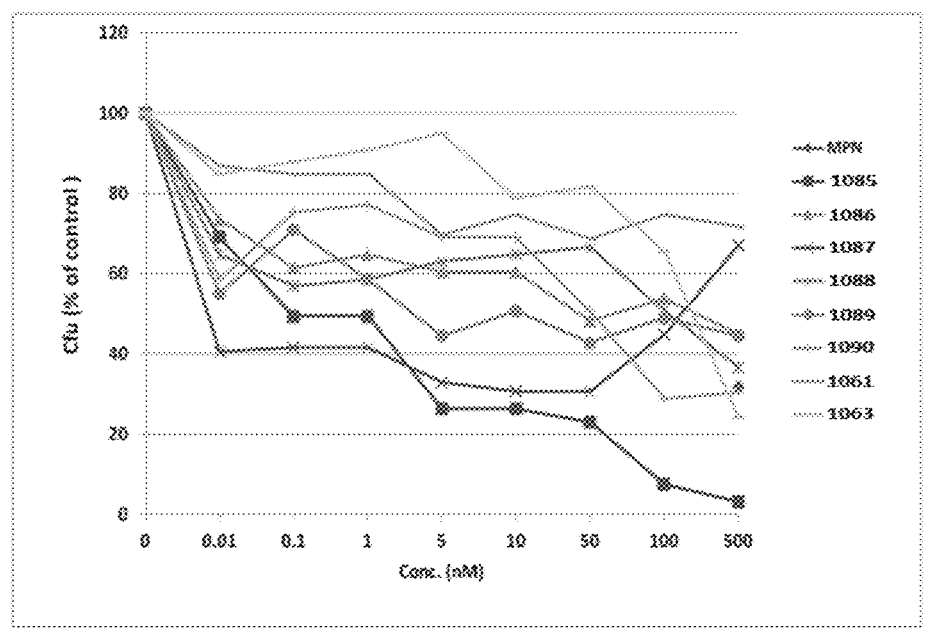
FIG. 1, depicts the effects of the compounds of the present invention in MYC-431 infected THP-1 macrophages

Accordingly, the present invention provides novel compound of Formula 1 as antitubercular agents.

The present invention relates to novel compounds of Formula (1):

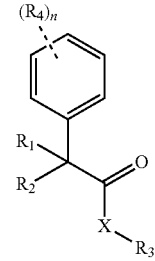

Formula 1 wherein,

X is selected from O or NH;

R$_1$ and R$_2$ are independently selected from hydrogen, deuterium, hydroxyl, C$_{1-10}$ straight chain or branched chain alkyl, 3-7 membered cycloalkyl, C$_{1-6}$alkoxy, aryl, amino, NH(alkyl), N(alkyl)$_2$, OCOR$_5$, heteroaryl containing 1-3 heteroatoms selected from the group comprising O, N or S; or R$_1$ and R$_2$ may combined to form an aryl or a heteroaryl ring containing 1-3 heteroatoms selected from the group comprising O, N or S;

R$_3$ is selected from hydrogen, hydroxyl, C$_{1-6}$ straight chain or branched chain alkyl, 3-7 membered cycloalkyl, C$_{1-6}$ alkoxy, aryl, aromatic or non-aromatic heterocyclic ring or fused heterocyclic ring selected from:

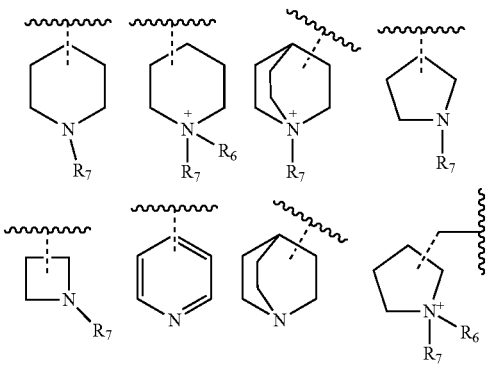

X may in conjunction with R3 form a 5-7 membered heterocyclic ring comprising 1-3 heteroatoms selected from group comprising N, O or S. The heterocyclic ring be further substituted with one or more lower alkyl groups, halogens, amino, NH(alkyl), N(alkyl)2, NH-aralkyl;

R4 is selected from a hydrogen, lower straight chain or branched alkyl, halogen, deuterium, C1-6 alkoxy, amino, NH(alkyl), N(alkyl)2, —COOR8, CONR8R9;

R5 is hydrogen, hydroxy, C1-6alkyl, C1-6alkoxy, amino, NH(alkyl), N(alkyl)2;

R6 and R7 are independently selected from the group comprising hydrogen, C1-10 alkyl, —COR8, —CH2OCOR8, —CH2OCONHR8R9, —COOR8, —CONR8R9, —SO2R8, aryl, aralkyl;
R8 and R9 are independently selected from the group comprising hydrogen, or C1-6 straight chain or branched chain alkyl;
n is 1, 2, or 3;
and salts, hydrates and stereoisomers thereof.

Further, the present invention relates to novel compounds of Formula (1):

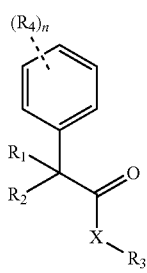

Formula 1 wherein
X is NH;
$R_1$ and $R_2$ are selected from hydrogen, hydroxyl, $C_{1-10}$ alkyl, $C_{1-6}$alkoxy;
$R_3$ is selected from substituted aromatic or non-aromatic heterocyclic ring or fused heterocyclic ring selected from:

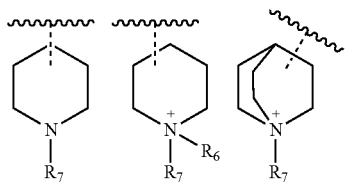

$R_4$ is selected from hydrogen, deuterium, halogen, $C_{1-6}$ straight chain or branched chain alkyl, $C_{1-6}$ alkoxy, amino, NH(alkyl), N(alkyl)$_2$;
$R_6$ and $R_7$ are independently selected from hydrogen, $C_{1-10}$ alkyl, —COR$_8$, —CH$_2$OCOR$_8$, —CH$_2$OCONHR$_8$R$_9$, —COOR$_8$, —CONR$_8$R$_9$, —SO$_2$R$_8$, phenyl, benzyl;
$R^8$ and $R^9$ are independently selected from hydrogen or $C_{1-6}$ straight chain or branched chain alkyl;
n is 1, 2 or 3.
and salts, hydrates and stereoisomers thereof.

The term "alkyl" refers to a linear or branched saturated monovalent hydrocarbon, wherein the alkylene may optionally be substituted as described herein. The term "alkyl" also encompasses both linear and branched alkyl, unless otherwise specified. In certain embodiments, the alkyl is a linear saturated monovalent hydrocarbon that has the specified number of carbon atoms, or branched saturated monovalent hydrocarbon of specified number of carbon atoms. As used herein, linear C1-C6 and branched C3-C6 alkyl groups are also referred as "lower alkyl." Examples of alkyl groups include, but are not limited to, methyl, ethyl, propyl (including allisomeric forms), n-propyl, isopropyl, butyl (including all isomeric forms), n-butyl, isobutyl, sec-butyl, t-butyl, pentyl (including all isomeric forms), and hexyl (including all isomeric forms). For example, C1-C6 alkyl refers to a linear saturated monovalent hydrocarbon of 1 to 6 carbon atoms or a branched saturated monovalent hydrocarbon of 3 to 6 carbon atoms.

The term "aryl" refers to a monocyclic aromatic group and/or multicyclic monovalent aromatic group that contain at least one aromatic hydrocarbon ring. In certain embodiments, the aryl has from 6 to 20 (C6-C20), from 6 to 15 (C6-C15), or from 6 to 10 (C6-C10) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "alkoxy" refers to the group R'O— wherein R' is alkyl. The term "lower alkoxy" refers to alkoxy groups having from 1 to 3 carbon atoms; examples include methoxy, ethoxy, isopropoxy, and the like.

The term "cycloalkyl" as used herein refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double bonds in the ring.

Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Unless otherwise stated, cycloalkyl groups are unsubstituted. A "substituted cycloalkyl" group can be substituted with one or more moieties selected from halo, hydroxy, amino, alkylamino, nitro, cyano, and alkoxy.

The term "aralkyl" or "aryl-alkyl" refers to a monovalent alkyl group substituted with aryl. In certain embodiments, the alkyl and aryl moieties are optionally substituted as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group may contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groupsinclude, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term heteroaralkyl refers to an aralkyl group as defined above, in which one or more (preferably 1, 2, 3 or 4) carbon atoms have been replaced by an oxygen, nitrogen, silicon, selenium, phosphorus, boron or sulphur atom (preferably oxygen, sulphur or nitrogen), that is to say groups that in accordance with the above definitions contain both aryl or heteroaryl and alkyl, alkenyl, alkynyl and/or heteroalkyl and/or cycloalkyl and/or heterocycloalkyl groups. A heteroaralkyl group preferably contains one or two aromatic ring systems (1 or 2 rings) with from 5 or 6 to 10 carbon atoms and one or two alkyl, alkenyl and/or alkynyl groups having from 1 or 2 to 6 carbon atoms and/or a cycloalkyl group having 5 or 6 ring carbon atoms, with 1, 2, 3 or 4 of those carbon atoms having been replaced by oxygen, sulphur or nitrogen atoms. Examples are aryl-heteroalkyl, aryl-heterocycloalkyl, aryl-heterocycloalkenyl, arylalkyl-heterocycloalkyl, arylalkenyl-heterocycloalkyl, arylalkynyl-heterocycloalkyl, arylalkyl-heterocycloalkenyl, heteroarylalkyl, heteroarylalkenyl, heteroarylalkynyl, heteroaryl-heteroalkyl, heteroarylcyclo-alkyl, heteroarylcycloalkenyl, heteroaryl-heterocycloalkyl, heteroaryl-heterocycloalkenyl, heteroarylalkylcycloalkyl, _g_heteroarylalkyl-heterocycloalkenyl, heteroaryl-heteroalkyl-cycloalkyl, heteroaryl-heteroalkylcycloalkenyl and hetero-aryl-heteroalkyl-heterocycloalkyl groups, the cyclic groups being saturated or mono-, di- or tri-unsaturated. Specific examples are the tetrahydroisoquinolinyl, benzoyl, 2- or 3-ethylindolyl, 4-methylpyridino, 2-, 3- or 4-methoxyphenyl, 4-ethoxyphenyl and 2-, 3- or 4-carboxylphenylalkyl groups.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic compounds include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, p-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "halogen", "halide" or "halo" refers to fluorine, chlorine, bromine, and iodine.

The term "heteroatom" as used herein means an atom of any element other than carbon or hydrogen. Preferred heteroatoms are nitrogen, oxygen, sulfur, phosphorus and selenium.

The term "aromatic", as used herein, refers to an unsaturated cyclic moiety that has an aromatic character. The term is intended to encompass both hydrocarbon aromatic compounds and heteroaromatic compounds. The terms "hydrocarbon aromatic ring" or "hydrocarbon aromatic compound" refer to an aromatic ring or compound in which the aromatic moieties have only carbon and hydrogen atoms. The terms "heteroaromatic ring" or "heteroaromatic compound' refer to an aromatic ring or compound wherein in at least one aromatic moiety one or more of the carbon atoms within the cyclic group has been replaced by another atom, such as nitrogen, oxygen, sulfur, or the like.

The term "non-aromatic", as used herein, refers to a cyclic moiety, that may be unsaturated, but that does not have an aromatic character.

The term "substituted" refers to where hydrogen radical on a molecule has been replaced by another atom radical, a functional group radical or a moiety radical; these radicals being generally referred to as "substituents."

The term "optionally substituted" is intended to mean that a group, such as an alkyl, alkylene, alkenyl, alkenylene, alkynyl, alkynylene, alkoxy, alkylamino, dialkylamino, carboxamido, cycloalkyl, cycloalkylene, aryl, arylene, heteroaryl, heteroarylene, heterocyclyl, or heterocyclylene, may be substituted with one or more substituents independently selected from, e.g., (a) C1-C6 alkyl, C2-C6 alkenyl, C2-C6 alkynyl, C3-C7 cycloalkyl, C6-C14 aryl, C7-C15aralkyl, heteroaryl, and heterocyclyl, each optionally substituted with one or more substituents; and (b) halo, cyano (—CN), nitro (—N02), —C(O)R3, —C(O)OR3, —C(O)NRbRC, —C(NR3)NR)RC, —OR3, —OC(O)R3, —OC(O)OR3, —OC(O)NRbRC, —OC(=NR3)NR)RC, —OS(O)R3, —OS(O)2R3, —OS(O)NRbRC, —OS(O) 2NRbRc, —NRbRc, —NR3C(O)Rd, —NR3C(O)ORd, —NR3C(O)NRbRC, —NR3C(=NRd)NRbRC, —NR3 S(O)Rd, —NR3 S(O)2Rd, —NR3 S(O)NRbRC, —NR3 S(O)NRbRc, —SR3, —S(O)R3, —S(O)2R3, —S(O) NRbRC, and —S(O)2NRbRC, wherein each R3, Rb, Re, and Rd is independently (i) hydrogen; (ii) C1-C6 alkyl, C2-C6 alkenyl, C2-C6 alkynyl, C3-C7cycloalkyl, C6-C14 aryl, C7-C15 aralkyl, heteroaryl, or heterocyclyl, each optionally substituted with one or more substituents; or (iii) Rb and Re together with the N atom to which they are attached form heteroaryl or heterocyclyl, optionally substituted with one or more, in one embodiment, one, two, three, or four, substituents. As used herein, all groups that may be substituted are "optionally substituted," unless otherwise specified.

The use of terms "a" and "an" and "the" and similar references in the context of describing the invention (especially in the context of the following claims) are to be construed to cover both the singular and the plural, unless otherwise indicated herein or clearly contraindicated by context.

The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise a basic moiety such as an amino group). Also included herein are quaternary ammonium salts such as alkyl ammonium salts. Pharmaceutically acceptable (i.e., non-toxic, physiologically acceptable) salts are preferred.

The term "pharmaceutically acceptable salts" refers to the acid addition salt compound formed with a suitable acid selected from an inorganic acid such as hydrochloric acid, hydrobromic acid; or an organic acid such as benzene sulfonic acid, maleic acid, oxalic acid, fumaric acid, succinic acid, p-toluenesulfonic acid and malic acid.

The term "hydrate" as used herein designates a crystalline molecular compound in which water molecules are incorporated into the crystal lattice. Generally speaking, a hydrate thus designates a crystalline form of a molecular compound, whereby the only further molecules incorporated into the crystal lattice are water molecules.

The term "stereoisomer's" refers to at least two compounds having the same molecular formula and connectivity of atoms, but having a different arrangement of atoms in a three-dimensional space. In view of the present disclosure, a stereoisomer can be, for example, an enantiomer, a diastereomer, or a meso compound.

The term "prophylactic" as used herein refers variously to medicaments, amounts or quantities, methods, uses and effects, etc., that prevent and/or aid in preventing infections.

The term "therapeutic" as used herein refers to preventing, ameliorating, treating, improving, or curing a disease or condition.

The term "Directly Observed Treatment Short-Course" (DOTS) refers to treatment regimen consisting of a four-drug such as Rifampicin, Isoniazid, Ethambutol and Pyrazinamide) intensive phase of two months, followed by a two-drug (Rifampicin and Isoniazid) continuation phase of four months.

The term "Multidrug resistance Tuberculosis" (MDR-TB) as used herein refers to tuberculosis which are resistant to at least isoniazid (INH) and rifampicin (RMP), the two most powerful first-line treatment anti-Tuberculosis drugs.

The term "Extensively drug resistance Tuberculosis" (XDR-TB) as used herein refers to the tuberculosis which are resistant to at least three of the six classes of second line anti-tuberculosis drugs as well as isoniazid and rifampicin, plus any fluoroquinolone and at least one of three injectable second-line drugs such as amikacin, kanamycin, or capreomycin.

The term "Totally Drug Resistance Tuberculosis" (TDR-TB) as used herein refers to the tuberculosis which are resistant to all first and second line drugs tested such as isoniazid, rifampicin, streptomycin, ethambutol, pyrazinamide, ethionamide, para-aminosalicylic acid, cycloserine, ofloxacin, amikacin, ciprofloxacin, capreomycin, kanamycin.

The term "H37Rv" as used herein refers to a pathogenic *M. tuberculosis* strain that has been sequenced.

The term "JAL2287" as used herein refers to the MDR (multi drug resistant) strain of *M. tuberculosis*

The term "MYC431" as used herein refers to the XDR (extensive drug resistant) strain of *M. tuberculosis*

The term "GPR109A" as used herein refers to the G-protein coupled receptor GPR109A.

The present invention provides compound represented by formula (1) that inhibits *mycobacterium* colony growth alone or in combination with DOTS (Directly Observed Treatment Short Course) therapy.

The compounds of the present invention may be illustrated but not limited to the examples as provided at Table 1.

TABLE 1

| Illustrative compounds of present invention | | |
|---|---|---|
| Chemical No. | Chemical Structure | Chemical Name |
| 1001 | 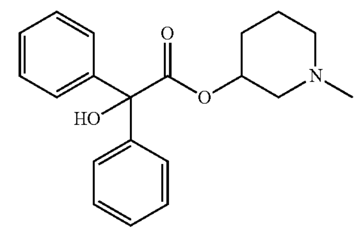 [SMILES: CN1CCCC(OC(=O)C(O)(c2ccccc2)c2ccccc2)C1]  | l-Methylpiperidin-3-yl-2-hydroxy-2,2-diphenylacetate |
| 1002 | 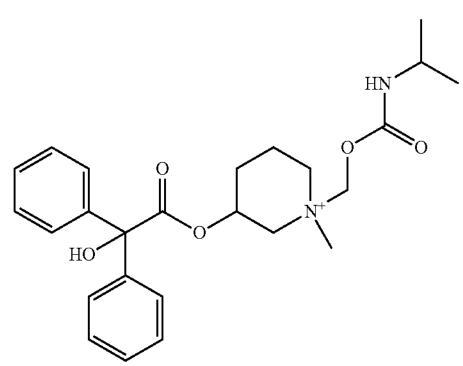 [SMILES: CC(C)NC(=O)OC[N+]1(C)CCCC(OC(=O)C(O)(c2ccccc2)c2ccccc2)C1]  | 3-(2-Hydroxy-2,2-diphenylacetoxy)-1-(((isopropylcarbamoyl)oxy)methyl)-1-methylpiperidin-1-ium |

TABLE 1-continued

Illustrative compounds of present invention

| Chemical No. | Chemical Structure | Chemical Name |
|---|---|---|
| 1003 | 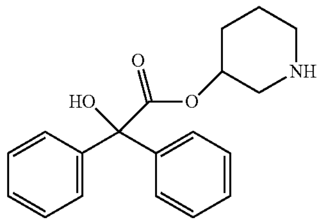 [SMILES: O=C(OC1CCCNC1)C(O)(c1ccccc1)c1ccccc1] | Piperidin-3-yl 2-hydroxy-2,2-diphenylacetate |
| 1004 | 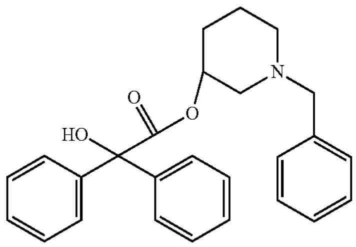 [SMILES: O=C(OC1CCCN(Cc2ccccc2)C1)C(O)(c1ccccc1)c1ccccc1] | 1-Benzylpiperidin-3-yl 2-hydroxy-2,2-diphenylacetate |
| 1005 | 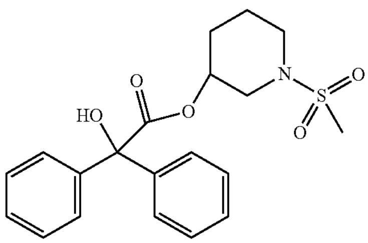 [SMILES: CS(=O)(=O)N1CCCC(OC(=O)C(O)(c2ccccc2)c2ccccc2)C1] | 1-(Methylsulfonyl)piperidin-3-yl 2-hydroxy-2,2-diphenylacetate |
| 1006 | 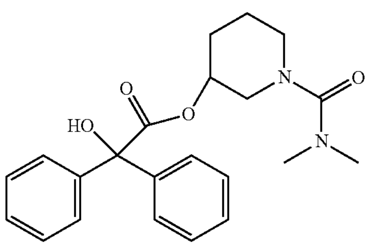 [SMILES: CN(C)C(=O)N1CCCC(OC(=O)C(O)(c2ccccc2)c2ccccc2)C1] | 1-(Dimethylcarbamoyl)piperidin-3-yl 2-hydroxy-2,2-diphenylacetate |
| 1007 | 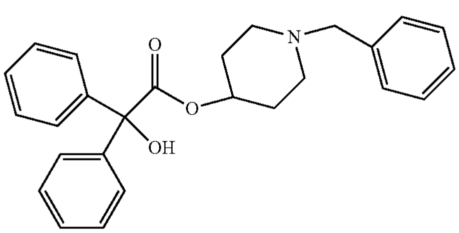 [SMILES: O=C(OC1CCN(Cc2ccccc2)CC1)C(O)(c1ccccc1)c1ccccc1] | 1-Benzylpiperidin-4-yl 2-hydroxy-2,2-diphenylacetate |
| 1008 | 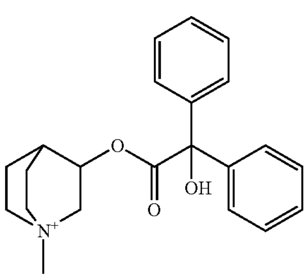 [SMILES: C[N+]12CCC(CC1)C(OC(=O)C(O)(c1ccccc1)c1ccccc1)C2] | 3-(2-Hydroxy-2,2-diphenylacetoxy)-1-methylquinuclidin-1-ium |

TABLE 1-continued

Illustrative compounds of present invention

| Chemical No. | Chemical Structure | Chemical Name |
|---|---|---|
| 1009 | 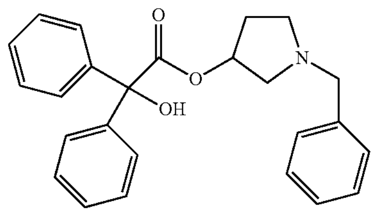 [SMILES: O=C(OC1CCN(Cc2ccccc2)C1)C(O)(c1ccccc1)c1ccccc1] | 1-Benzylpyrrolidin-3-yl 2-hydroxy-2,2-diphenylacetate |
| 1010 | 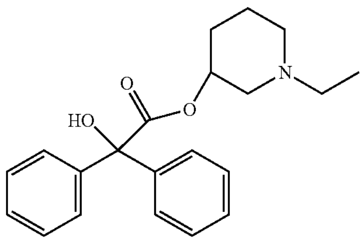 [SMILES: CCN1CCCC(OC(=O)C(O)(c2ccccc2)c2ccccc2)C1] | 1-Ethylpiperidin-3-yl 2-hydroxy-2,2-diphenylacetate |
| 1011 | 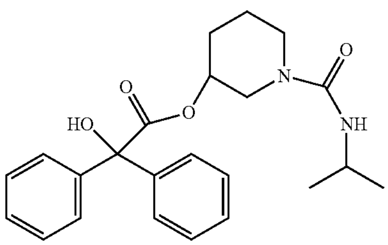 [SMILES: CC(C)NC(=O)N1CCCC(OC(=O)C(O)(c2ccccc2)c2ccccc2)C1] | 1-(Isopropylcarbamoyl)piperidin-3-yl 2-hydroxy-2,2-diphenylacetate |
| 1012 | 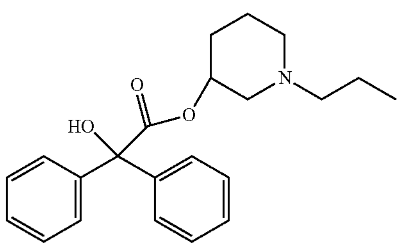 [SMILES: CCCN1CCCC(OC(=O)C(O)(c2ccccc2)c2ccccc2)C1] | 1-Propylpiperidin-3-yl 2-hydroxy-2,2-diphenylacetate |
| 1013 | 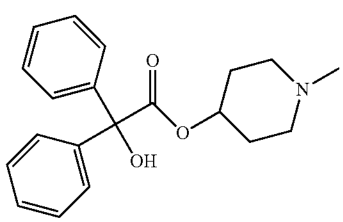 [SMILES: CN1CCC(OC(=O)C(O)(c2ccccc2)c2ccccc2)CC1] | 1-Methylpiperidin-4-yl 2-hydroxy-2,2-diphenylacetate |
| 1014 | 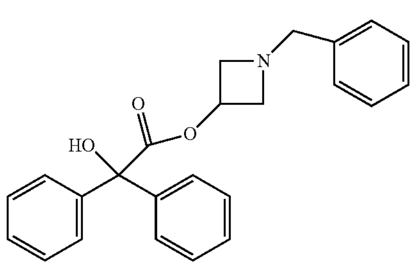 [SMILES: O=C(OC1CN(Cc2ccccc2)C1)C(O)(c1ccccc1)c1ccccc1] | 1-Benzylazetidin-3-yl 2-hydroxy-2,2-diphenylacetate |

TABLE 1-continued

Illustrative compounds of present invention

| Chemical No. | Chemical Structure | Chemical Name |
|---|---|---|
| 1015 | 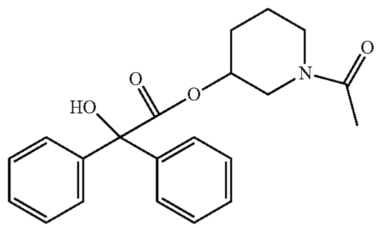 [SMILES: CC(=O)N1CCCC(OC(=O)C(O)(c2ccccc2)c2ccccc2)C1] | 1-Acetylpiperidin-3-yl 2-hydroxy-2,2-diphenylacetate |
| 1016 | 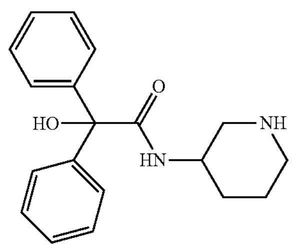 [SMILES: O=C(NC1CCCNC1)C(O)(c1ccccc1)c1ccccc1] | 2-Hydroxy-2,2-diphenyl-N-(piperidin-3-yl)acetamide |
| 1017 | 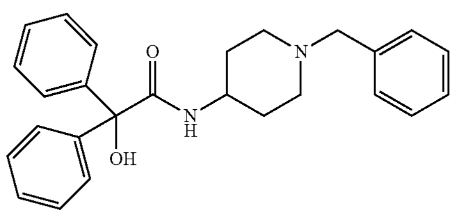 [SMILES: O=C(NC1CCN(Cc2ccccc2)CC1)C(O)(c1ccccc1)c1ccccc1] | N-(1-Benzylpiperidin-4-yl)-2-hydroxy-2,2-diphenylacetamide |
| 1018 | 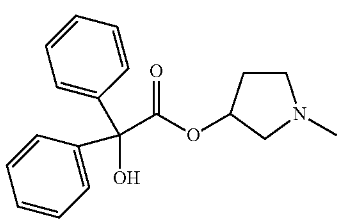 [SMILES: CN1CCC(OC(=O)C(O)(c2ccccc2)c2ccccc2)C1] | 1-Methylpyrrolidin-3-yl 2-hydroxy-2,2-diphenylacetate |
| 1019 | 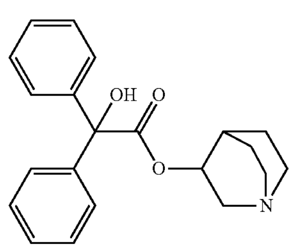 [SMILES: O=C(OC1CN2CCC1CC2)C(O)(c1ccccc1)c1ccccc1] | Quinuclidin-3-yl 2-hydroxy-2,2-diphenylacetate |
| 1020 | 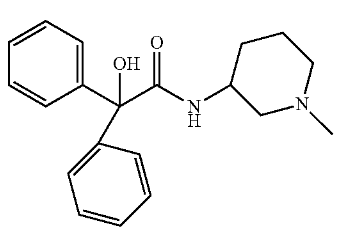 [SMILES: CN1CCCC(NC(=O)C(O)(c2ccccc2)c2ccccc2)C1] | 2-Hydroxy-N-(1-methylpiperidin-3-yl)-2,2-diphenylacetamide |

TABLE 1-continued

Illustrative compounds of present invention

| Chemical No. | Chemical Structure | Chemical Name |
|---|---|---|
| 1021 | 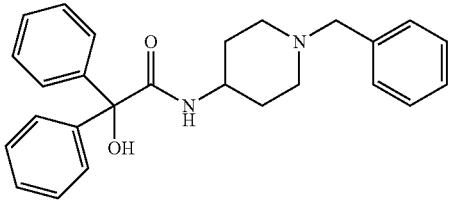 [SMILES: O=C(NC1CCN(Cc2ccccc2)CC1)C(O)(c1ccccc1)c1ccccc1] | N-(1-Benzylpiperidin-4-yl)-2-hydroxy-2,2-diphenylacetamide |
| 1022 | 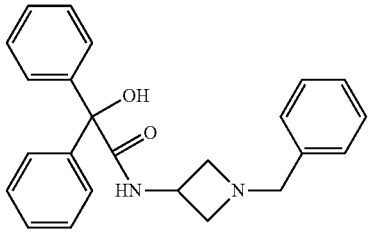 [SMILES: O=C(NC1CN(Cc2ccccc2)C1)C(O)(c1ccccc1)c1ccccc1] | N-(1-Benzylazetidin-3-yl)-2-hydroxy-2,2-diphenylacetamide |
| 1023 | 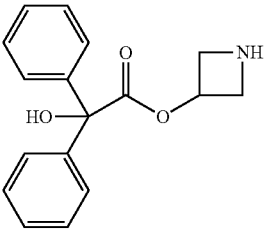 [SMILES: O=C(OC1CNC1)C(O)(c1ccccc1)c1ccccc1] | Azetidin-3-yl 2-hydroxy-2,2-diphenylacetate |
| 1024 | 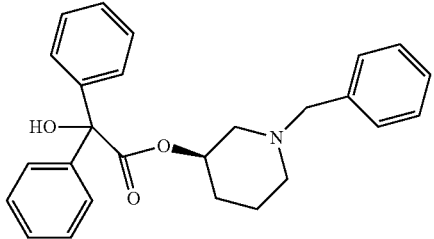 [SMILES: O=C(O[C@@H]1CCCN(Cc2ccccc2)C1)C(O)(c1ccccc1)c1ccccc1] | (S)-1-Benzylpiperidin-3-yl 2-hydroxy-2,2-diphenylacetate |
| 1025 | 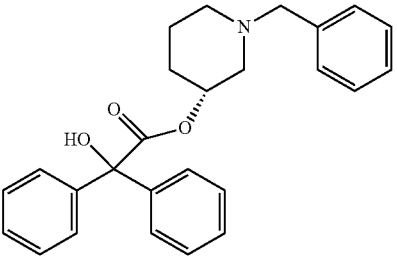 [SMILES: O=C(O[C@@H]1CCCN(Cc2ccccc2)C1)C(O)(c1ccccc1)c1ccccc1] | (R)-1-Benzylpiperidin-3-yl 2-hydroxy-2,2-diphenylacetate |
| 1026 | 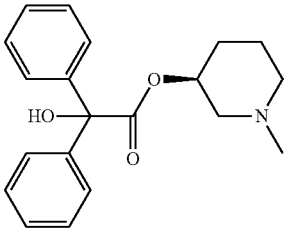 [SMILES: CN1CCC[C@H](OC(=O)C(O)(c2ccccc2)c2ccccc2)C1] | (S)-1-Methylpiperidin-3-yl 2-hydroxy-2,2-diphenylacetate |

TABLE 1-continued

Illustrative compounds of present invention

| Chemical No. | Chemical Structure | Chemical Name |
|---|---|---|
| 1027 | 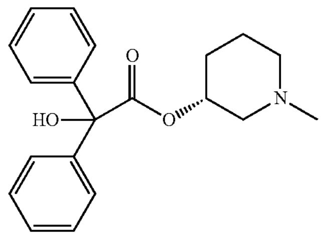 [SMILES: CN1CCC[C@@H](OC(=O)C(O)(c2ccccc2)c2ccccc2)C1] | (R)-1-Methylpiperidin-3-yl 2-hydroxy-2,2-diphenylacetate |
| 1028 | 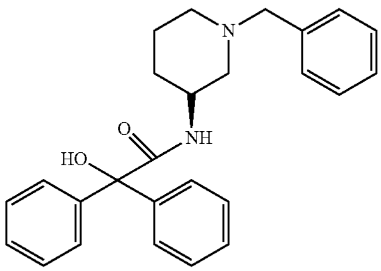 | (R)-N-(1-Benzylpiperidin-3-yl)-2-hydroxy-2,2-diphenylacetamide |
| 1029 | 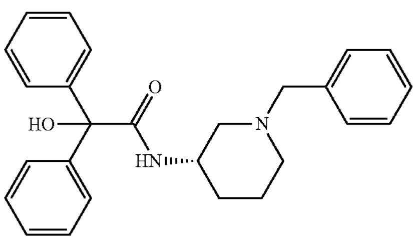 [SMILES: O=C(N[C@H]1CCCN(Cc2ccccc2)C1)C(O)(c1ccccc1)c1ccccc1] | (R)-N-(1-Benzylpiperidin-3-yl)-2-hydroxy-2,2-diphenylacetamide |
| 1030 | 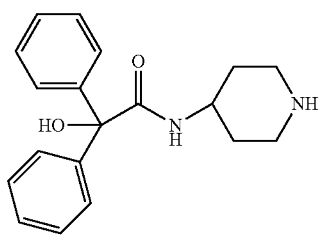 [SMILES: O=C(NC1CCNCC1)C(O)(c1ccccc1)c1ccccc1] | 2-Hydroxy-2,2-diphenyl-N-(piperidin-4-yl)acetamide |
| 1031 | 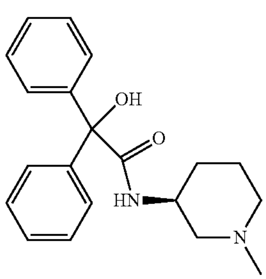 [SMILES: CN1CCC[C@H](NC(=O)C(O)(c2ccccc2)c2ccccc2)C1] | (S)-2-Hydroxy-N-(1-methylpiperidin-3-yl)-2,2-diphenylacetamide |
| 1032 | 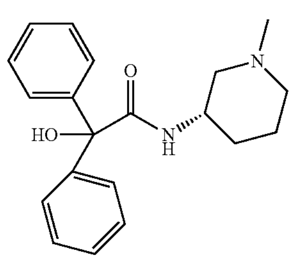 [SMILES: CN1CCC[C@H](NC(=O)C(O)(c2ccccc2)c2ccccc2)C1] | (R)-2-Hydroxy-N-(1-methylpiperidin-3-yl)-2,2-diphenylacetamide |

TABLE 1-continued

Illustrative compounds of present invention

| Chemical No. | Chemical Structure | Chemical Name |
|---|---|---|
| 1033 | 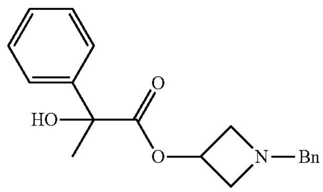 [SMILES: CC(O)(C(=O)OC1CN(Cc2ccccc2)C1)c1ccccc1] | 1-Benzylazetidin-3-yl 2-hydroxy-2-phenylpropanoate |
| 1034 | 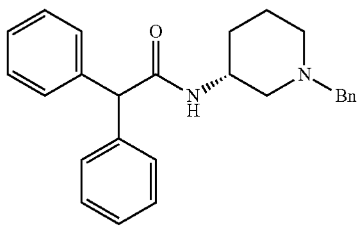 [SMILES: O=C(N[C@@H]1CCCN(Cc2ccccc2)C1)C(c1ccccc1)c1ccccc1] | (R)-N-(1-Benzylpiperidin-3-yl)-2,2-diphenylacetamide |
| 1035 | 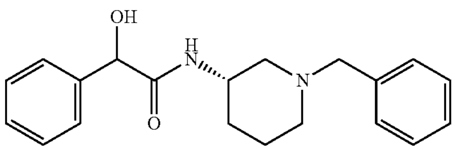 [SMILES: O=C(N[C@H]1CCCN(Cc2ccccc2)C1)C(O)c1ccccc1] | N-((S)-1-Benzylpiperidin-3-yl)-2-hydroxy-2-phenylacetamide |
| 1036 | 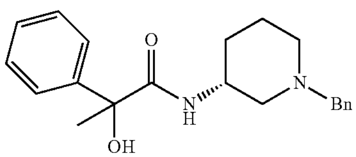 [SMILES: CC(O)(C(=O)N[C@@H]1CCCN(Cc2ccccc2)C1)c1ccccc1] | N-((R)-1-Benzylpiperidin-3-yl)-2 hydroxy-2-phenylpropanamide |
| 1037 | 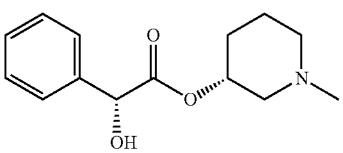 [SMILES: CN1CCC[C@@H](OC(=O)[C@H](O)c2ccccc2)C1] | (R)-(R)-1-Methylpiperidin-3-yl 2-hydroxy-2-phenylacetate |
| 1038 | 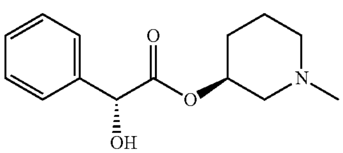 [SMILES: CN1CCC[C@H](OC(=O)[C@H](O)c2ccccc2)C1] | (R)-(S)-1-Methylpiperidin-3-yl 2-hydroxy-2-phenylacetate |
| 1039 | 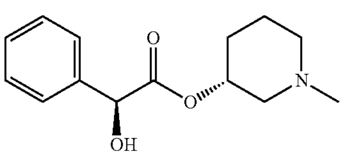 [SMILES: CN1CCC[C@@H](OC(=O)[C@@H](O)c2ccccc2)C1] | (S)-(R)-1-Methylpiperidin-3-yl 2-hydroxy-2-phenylacetate |
| 1040 | 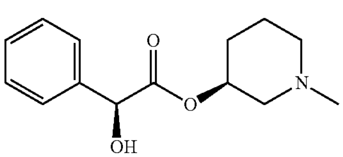 [SMILES: CN1CCC[C@H](OC(=O)[C@@H](O)c2ccccc2)C1] | (S)-(S)-1-Methylpiperidin-3-yl 2-hydroxy-2-phenylacetate |
| 1041 | 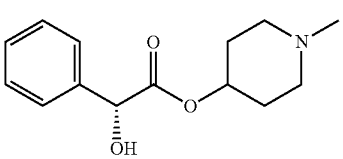 [SMILES: CN1CCC(OC(=O)[C@H](O)c2ccccc2)CC1] | (R)-1-Methylpiperidin-4-yl 2-hydroxy-2-phenylacetate |

TABLE 1-continued

Illustrative compounds of present invention

| Chemical No. | Chemical Structure | Chemical Name |
|---|---|---|
| 1042 | 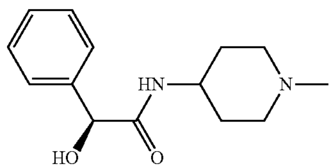 [SMILES: CN1CCC(NC(=O)[C@@H](O)c2ccccc2)CC1] | (S)-2-Hydroxy-N-(1-methylpiperidin-4-yl)-2-phenylacetamide |
| 1043 | 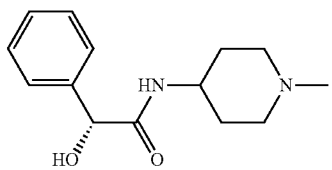 [SMILES: CN1CCC(NC(=O)[C@H](O)c2ccccc2)CC1] | (R)-2-Hydroxy-N-(1-methylpiperidin-4-yl)-2-phenylacetamide |
| 1044 | 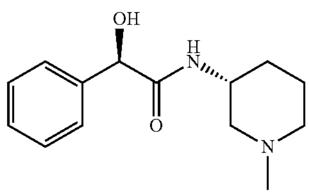 [SMILES: CN1CCC[C@@H](NC(=O)[C@H](O)c2ccccc2)C1] | (R)-2-Hydroxy-N-((R)-1-methylpiperidin-3-yl)-2-phenylacetamide |
| 1045 | 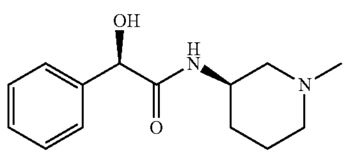 [SMILES: CN1CCC[C@@H](NC(=O)[C@H](O)c2ccccc2)C1] | (R)-2-Hydroxy-N-((S)-1-methylpiperidin-3-yl)-2-phenylacetamide |
| 1046 | 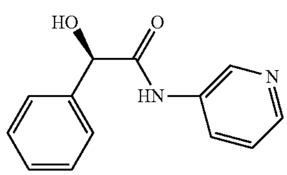 [SMILES: O=C(Nc1cccnc1)[C@H](O)c1ccccc1] | (S)-2-Hydroxy-2-phenyl-N-(pyridin-3-yl)acetamide |
| 1047 | 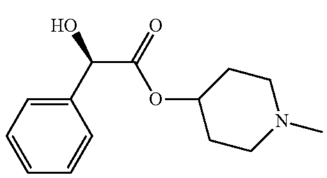 [SMILES: CN1CCC(OC(=O)[C@H](O)c2ccccc2)CC1] | (S)-1-Methylpiperidin-4-yl 2-hydroxy-2-phenylacetate |
| 1048 | 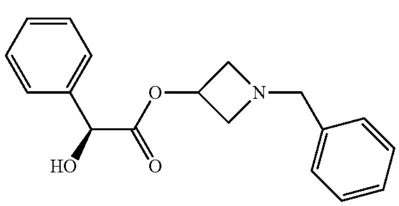 [SMILES: O=C(OC1CN(Cc2ccccc2)C1)[C@@H](O)c1ccccc1] | (S)-1-Benzylazetidin-3-yl 2-hydroxy-2-phenylacetate |
| 1049 | 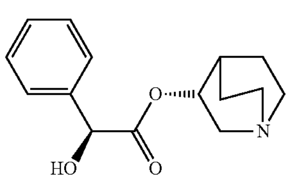 | (S)-(R)-Quinuclidin-3-yl 2-hydroxy-2-phenylacetate |

TABLE 1-continued

Illustrative compounds of present invention

| Chemical No. | Chemical Structure | Chemical Name |
|---|---|---|
| 1050 | 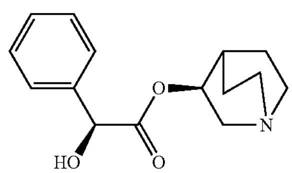 [SMILES: O=C(O[C@@H]1CN2CCC1CC2)[C@@H](O)c1ccccc1] | (S)-(S)-Quinuclidin-3-yl 2-hydroxy-2-phenylacetate |
| 1051 | 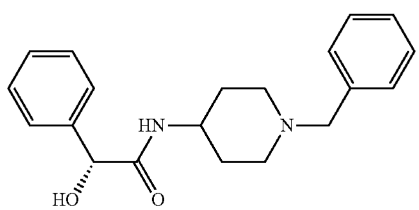 [SMILES: O=C(NC1CCN(Cc2ccccc2)CC1)[C@H](O)c1ccccc1] | (R)-N-(1-Benzylpiperidin-4-yl)-2-hydroxy-2-phenylacetamide |
| 1052 | 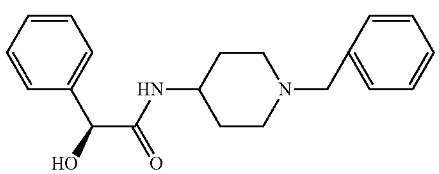 [SMILES: O=C(NC1CCN(Cc2ccccc2)CC1)[C@@H](O)c1ccccc1] | (S)-N-(1-Benzylpiperidin-4-yl)-2-hydroxy-2-phenylacetamide |
| 1053 | 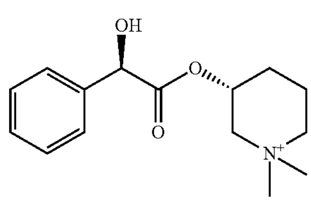 [SMILES: C[N+]1(C)CCC[C@@H](OC(=O)[C@H](O)c2ccccc2)C1] | (R)-3-((R)-2-Hydroxy-2-phenylacetoxy)-1,1-dimethylpiperidin-1-ium |
| 1054 | 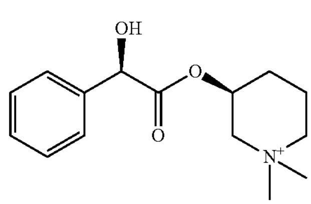 [SMILES: C[N+]1(C)CCC[C@H](OC(=O)[C@H](O)c2ccccc2)C1] | (S)-3-((R)-2-Hydroxy-2-phenylacetoxy)-1,1-dimethylpiperidin-1-ium |
| 1055 | 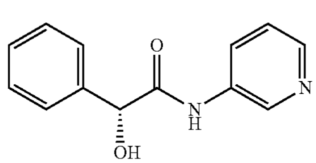 [SMILES: O=C(Nc1cccnc1)[C@H](O)c1ccccc1] | (R)-2-Hydroxy-2-phenyl-N-(pyridin-3-yl)acetamide |
| 1056 | 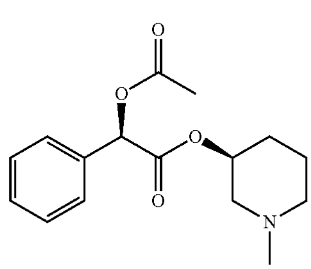 [SMILES: CC(=O)O[C@@H](C(=O)O[C@H]1CCCN(C)C1)c1ccccc1] | (R)-(S)-1-Methylpiperidin-3-yl 2-acetoxy-2-phenylacetate |

TABLE 1-continued

Illustrative compounds of present invention

| Chemical No. | Chemical Structure | Chemical Name |
|---|---|---|
| 1057 | 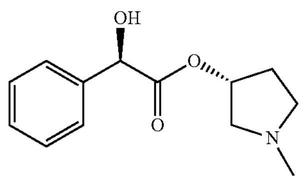 [SMILES: CN1CC[C@@H](OC(=O)[C@H](O)c2ccccc2)C1] | (R)-(R)-1-Methylpyrrolidin-3-yl 2-hydroxy-2-phenylacetate |
| 1058 | 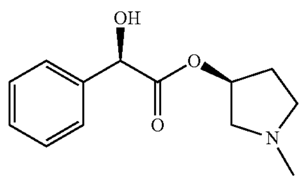 [SMILES: CN1CC[C@H](OC(=O)[C@H](O)c2ccccc2)C1] | (R)-(S)-1-Methylpyrrolidin-3-yl 2-hydroxy-2-phenylacetate |
| 1059 | 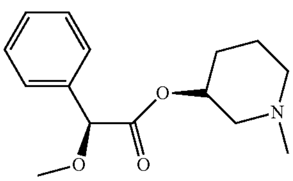 | (S)-(R)-1-Methylpiperidin-3-yl 2-methoxy-2-phenylacetate |
| 1060 | 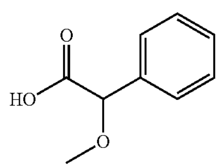 | 2-Methoxy-2-phenylacetic acid |
| 1061 | 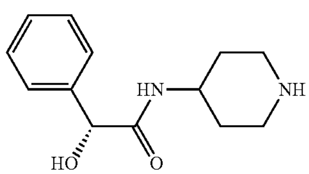 [SMILES: O=C(NC1CCNCC1)[C@H](O)c1ccccc1] | (R)-2-Hydroxy-2-phenyl-N-(piperidin-4-yl)acetamide |
| 1062 | 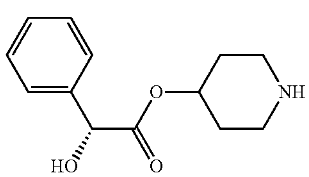 [SMILES: O=C(OC1CCNCC1)[C@H](O)c1ccccc1] | (R)-Piperidin-4-yl 2-hydroxy-2-phenylacetate |
| 1063 | 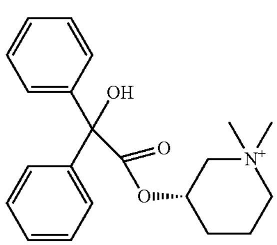 [SMILES: C[N+]1(C)CCC[C@H](OC(=O)C(O)(c2ccccc2)c2ccccc2)C1] | (R)-3-(2-Hydroxy-2,2-diphenylacetoxy)-1,1-dimethylpiperidin-1-ium |

TABLE 1-continued

Illustrative compounds of present invention

| Chemical No. | Chemical Structure | Chemical Name |
|---|---|---|
| 1064 | 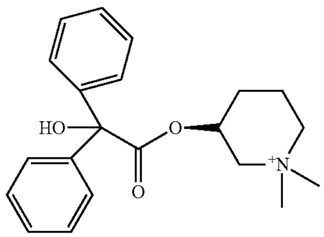 | (R)-3-(2-Hydroxy-2,2-diphenylacetoxy)-1,1-dimethylpiperidin-1-ium |
| 1065 | 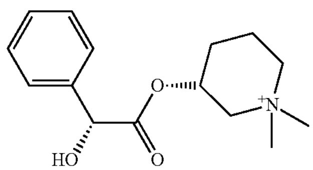 | (R)-3-((R)-2-Hydroxy-2-phenylacetoxy)-1,1-dimethylpiperidin-1-ium |
| 1066 | 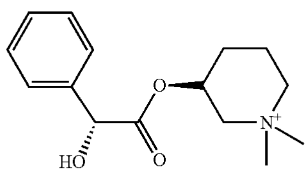 | (R)-3-((R)-2-Hydroxy-2-phenylacetoxy)-1,1-dimethylpiperidin-1-ium |
| 1067 | 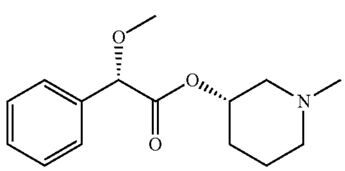 [SMILES: CO[C@H](C(=O)O[C@H]1CCCN(C)C1)c1ccccc1] | (S)-(R)-1-Methylpiperidin-3-yl 2-methoxy-2-phenylacetate |
| 1068 | 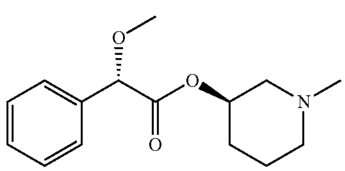 [SMILES: CO[C@H](C(=O)O[C@@H]1CCCN(C)C1)c1ccccc1] | (S)-(S)-1-Methylpiperidin-3-yl 2-methoxy-2-phenylacetate |
| 1069 | 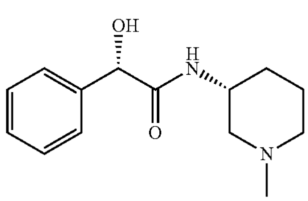 [SMILES: CN1CCC[C@@H](NC(=O)[C@@H](O)c2ccccc2)C1] | (S)-2-Hydroxy-N-((R)-1-methylpiperidin-3-yl)-2-phenylacetamide |
| 1070 | 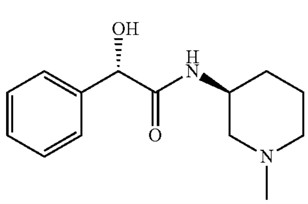 [SMILES: CN1CCC[C@H](NC(=O)[C@@H](O)c2ccccc2)C1] | (S)-2-Hydroxy-N-((S)-1-methylpiperidin-3-yl)-2-phenylacetamide |

TABLE 1-continued

Illustrative compounds of present invention

| Chemical No. | Chemical Structure | Chemical Name |
|---|---|---|
| 1071 | 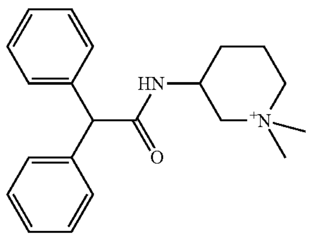 [SMILES: C[N+]1(C)CCCC(NC(=O)C(c2ccccc2)c2ccccc2)C1] | 3-(2,2-Diphenylacetamido)-1,1-dimethylpiperidin-1-ium |
| 1072 | 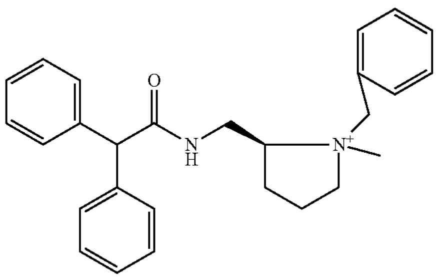 [SMILES: C[N+]1(Cc2ccccc2)CCC[C@H]1CNC(=O)C(c1ccccc1)c1ccccc1] | (2S)-1-Benzyl-2-((2,2-diphenylacetamido)methyl)-1-methylpyrrolidin-1-ium |
| 1073 | 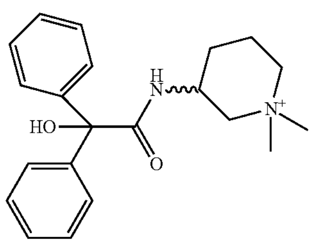 [SMILES: C[N+]1(C)CCCC(NC(=O)C(O)(c2ccccc2)c2ccccc2)C1] | 3-(2-Hydroxy-2,2-diphenylacetamido)-1,1-dimethylpiperidin-1-ium |
| 1074 | 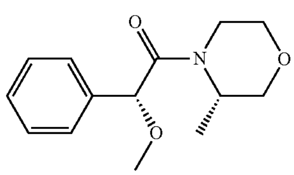 [SMILES: CO[C@@H](C(=O)N1CCOC[C@@H]1C)c1ccccc1] | (R)-2-Methoxy-1-((S)-3-methylmorpholino)-2-phenylethanone |
| 1075 | 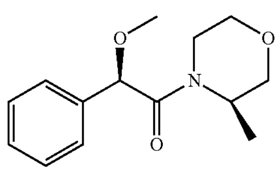 [SMILES: CO[C@@H](C(=O)N1CCOC[C@H]1C)c1ccccc1] | (R)-2-Methoxy-1-((R)-3-methylmorpholino)-2-phenylethanone |
| 1076 | 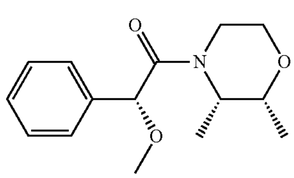 [SMILES: CO[C@@H](C(=O)N1CCO[C@H](C)[C@@H]1C)c1ccccc1] | (R)-1-((2R,3S)-2,3-Dimethylmorpholino)-2-methoxy-2-phenylethanone |
| 1077 | 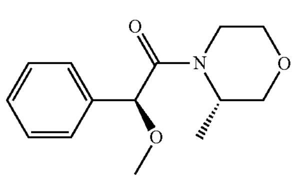 [SMILES: CO[C@H](C(=O)N1CCOC[C@@H]1C)c1ccccc1] | (S)-2-Methoxy-1-((S)-3-methylmorpholino)-2-phenylethanone |

TABLE 1-continued

Illustrative compounds of present invention

| Chemical No. | Chemical Structure | Chemical Name |
|---|---|---|
| 1078 | 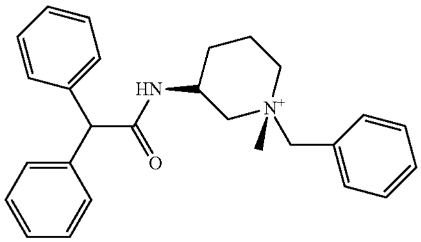 | (1R,3R)-1-Benzyl-3-(2,2-diphenylacetamido)-1-methylpiperidin-1-ium |
| 1079 | 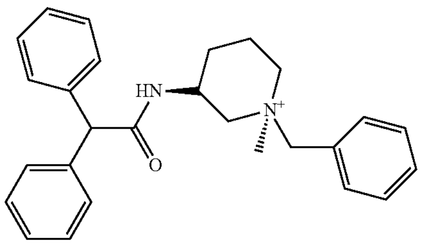 | (1S,3R)-1-Benzyl-3-(2,2-diphenylacetamido)-1-methylpiperidin-1-ium |
| 1080 | 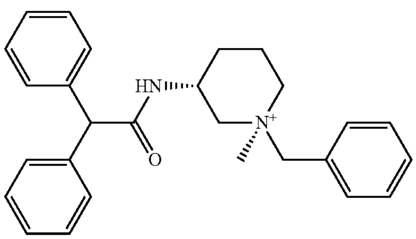 [SMILES: C[N@@+]1(Cc2ccccc2)CCC[C@@H](NC(=O)C(c2ccccc2)c2ccccc2)C1] | (1S,3R)-1-Benzyl-3-(2,2-diphenylacetamido)-1-methylpiperidin-1-ium |
| 1081 | 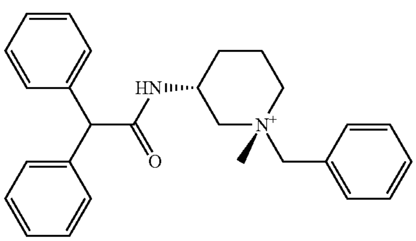 [SMILES: C[N@+]1(Cc2ccccc2)CCC[C@@H](NC(=O)C(c2ccccc2)c2ccccc2)C1] | (1R,3R)-1-Benzyl-3-(2,2-diphenylacetamido)-1-methylpiperidin-1-ium |
| 1082 | 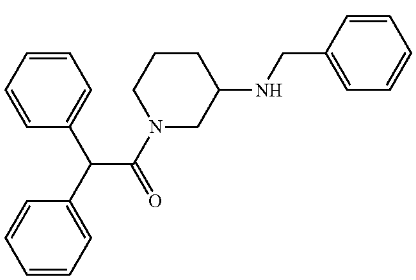 [SMILES: O=C(C(c1ccccc1)c1ccccc1)N1CCCC(NCc2ccccc2)C1] | 1-(3-(Benzylamino)piperidin-1-yl)-2,2-diphenylethanone |
| 1083 | 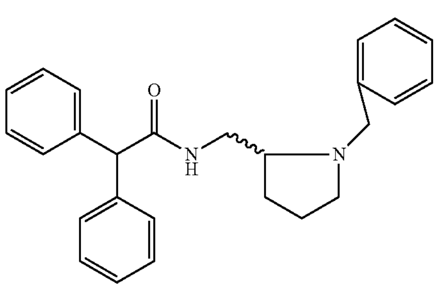 [SMILES: O=C(NCC1CCCN1Cc1ccccc1)C(c1ccccc1)c1ccccc1] | N-((1-Benzylpyrrolidin-2-yl)methyl)-2,2-diphenylacetamide |

TABLE 1-continued

Illustrative compounds of present invention

| Chemical No. | Chemical Structure | Chemical Name |
|---|---|---|
| 1084 | 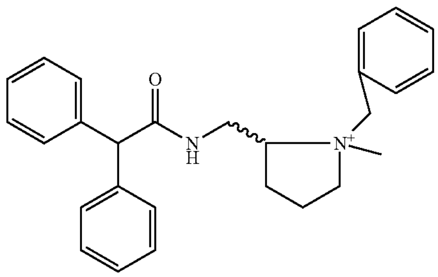 [SMILES: C[N+]1(Cc2ccccc2)CCCC1CNC(=O)C(c1ccccc1)c1ccccc1] | 1-Benzyl-2-((2,2-diphenylacetamido)methyl)-1-methylpyrrolidin-1-ium |
| 1085 | 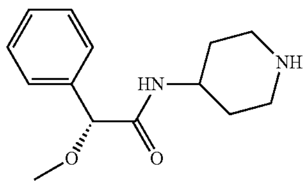 [SMILES: CO[C@@H](C(=O)NC1CCNCC1)c1ccccc1] | (R)-2-Methoxy-2-phenyl-N-(piperidin-4-yl)acetamide |
| 1086 | 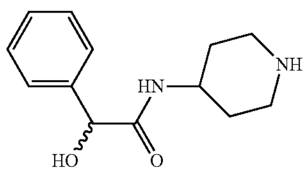 [SMILES: O=C(NC1CCNCC1)C(O)c1ccccc1] | 2-Hydroxy-2-phenyl-N-(piperidin-4-yl)acetamide |
| 1087 | 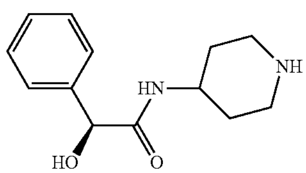 [SMILES: O=C(NC1CCNCC1)[C@@H](O)c1ccccc1] | (S)-2-Hydroxy-2-phenyl-N-(piperidin-4-yl)acetamide |
| 1088 | 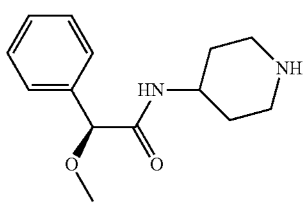 [SMILES: CO[C@H](C(=O)NC1CCNCC1)c1ccccc1] | (S)-2-Methoxy-2-phenyl-N-(piperidin-4-yl)acetamide |
| 1089 | 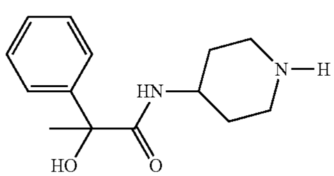 [SMILES: CC(O)(C(=O)NC1CCNCC1)c1ccccc1] | 2-Hydroxy-2-phenyl-N-(piperidin-4-yl)propanamide |
| 1090 | 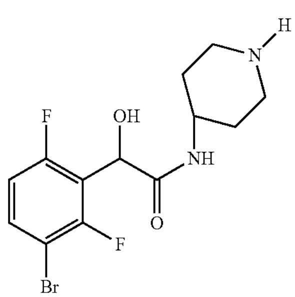 [SMILES: O=C(NC1CCNCC1)C(O)c1c(F)ccc(Br)c1F] | 2-(3-Bromo-2,6-difluorophenyl)-2-hydroxy-N-(piperidin-4-yl)acetamide |

TABLE 1-continued

Illustrative compounds of present invention

| Chemical No. | Chemical Structure | Chemical Name |
|---|---|---|
| 1091 | 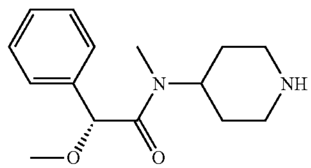 [SMILES: CO[C@@H](C(=O)N(C)C1CCNCC1)c1ccccc1] | (R)-2-Methoxy-N-methyl-2-phenyl-N-(piperidin-4-yl)acetamide |
| 1092 | 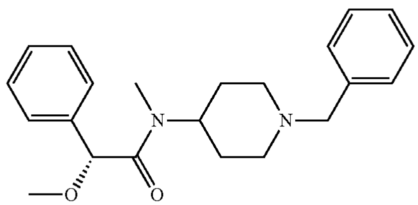 [SMILES: CO[C@@H](C(=O)N(C)C1CCN(Cc2ccccc2)CC1)c1ccccc1] | (R)-N-(1-Benzylpiperidin-4-yl)-2-methoxy-N-methyl-2-phenylacetamide |
| 1093 | 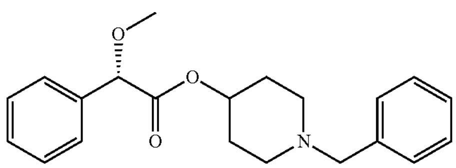 [SMILES: CO[C@H](C(=O)OC1CCN(Cc2ccccc2)CC1)c1ccccc1] | (S)-1-Benzylpiperidin-4-yl 2-methoxy-2-phenylacetate |
| 1094 | 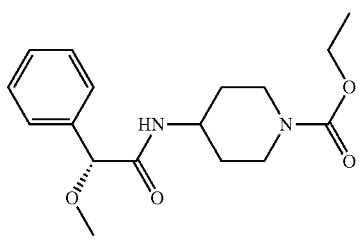 [SMILES: CCOC(=O)N1CCC(NC(=O)[C@H](OC)c2ccccc2)CC1] | (R)-Ethyl 4-(2-methoxy-2-phenylacetamido)piperidine-1-carboxylate |

The present invention also provides for compounds of formula (1) as below:

i. 1-methylpiperidin-3-yl-2-hydroxy-2,2-diphenylacetate;
ii. 3-(2-hydroxy-2,2-diphenylacetoxy)-1-(((isopropylcarbamoyl)oxy)methyl)-1-methylpiperidin-1-ium;
iii. piperidin-3-yl 2-hydroxy-2,2-diphenylacetate;
iv. 1-benzylpiperidin-3-yl 2-hydroxy-2,2-diphenylacetate;
v. 1-(methylsulfonyl)piperidin-3-yl 2-hydroxy-2,2-diphenylacetate;
vi. 1-(dimethylcarbamoyl)piperidin-3-yl 2-hydroxy-2,2-diphenylacetate;
vii. 1-benzylpiperidin-4-yl 2-hydroxy-2,2-diphenylacetate;
viii. 3-(2-hydroxy-2,2-diphenylacetoxy)-1-methylquinuclidin-1-ium;
ix. 1-benzylpyrrolidin-3-yl 2-hydroxy-2,2-diphenylacetate;
x. 1-ethylpiperidin-3-yl 2-hydroxy-2,2-diphenylacetate;
xi. 1-(isopropylcarbamoyl)piperidin-3-yl 2-hydroxy-2,2-diphenylacetate;
xii. 1-propylpiperidin-3-yl 2-hydroxy-2,2-diphenylacetate;
xiii. 1-methylpiperidin-4-yl 2-hydroxy-2,2-diphenylacetate;
xiv. 1-benzylazetidin-3-yl 2-hydroxy-2,2-diphenylacetate;
xv. 1-acetylpiperidin-3-yl 2-hydroxy-2,2-diphenylacetate;
xvi. 2-hydroxy-2,2-diphenyl-N-(piperidin-3-yl)acetamide;
xvii. N-(1-benzylpiperidin-4-yl)-2-hydroxy-2,2-diphenylacetamide;
xviii. 1-methylpyrrolidin-3-yl 2-hydroxy-2,2-diphenylacetate;
xix. quinuclidin-3-yl 2-hydroxy-2,2-diphenylacetate;
xx. 2-hydroxy-N-(1-methylpiperidin-3-yl)-2,2-diphenylacetamide;
xxi. N-(1-benzylpiperidin-4-yl)-2-hydroxy-2,2-diphenylacetamide;
xxii. N-(1-benzylazetidin-3-yl)-2-hydroxy-2,2-diphenylacetamide;
xxiii. azetidin-3-yl 2-hydroxy-2,2-diphenylacetate;
xxiv. (S)-1-benzylpiperidin-3-yl 2-hydroxy-2,2-diphenylacetate;
xxv. (R)-1-benzylpiperidin-3-yl 2-hydroxy-2,2-diphenylacetate;
xxvi. (S)-1-methylpiperidin-3-yl 2-hydroxy-2,2-diphenylacetate;
xxvii. (R)-1-methylpiperidin-3-yl 2-hydroxy-2,2-diphenylacetate;
xxviii. (R)—N-(1-benzylpiperidin-3-yl)-2-hydroxy-2,2-diphenylacetamide;
xxix. (R)—N-(1-benzylpiperidin-3-yl)-2-hydroxy-2,2-diphenylacetamide;
xxx. 2-hydroxy-2,2-diphenyl-N-(piperidin-4-yl)acetamide;

xxxi. (S)-2-hydroxy-N-(1-methylpiperidin-3-yl)-2,2-diphenylacetamide;
xxxii. (R)-2-hydroxy-N-(1-methylpiperidin-3-yl)-2,2-diphenylacetamide;
xxxiii. 1-benzylazetidin-3-yl 2-hydroxy-2-phenylpropanoate;
xxxiv. (R)—N-(1-benzylpiperidin-3-yl)-2,2-diphenylacetamide;
xxxv. N—((S)-1-benzylpiperidin-3-yl)-2-hydroxy-2-phenylacetamide;
xxxvi. N—((R)-1-benzylpiperidin-3-yl)-2-hydroxy-2-phenylpropanamide;
xxxvii. (R)—(R)-1-methylpiperidin-3-yl 2-hydroxy-2-phenylacetate;
xxxviii. (R)—(S)-1-methylpiperidin-3-yl 2-hydroxy-2-phenylacetate;
xxxix. (S)—(R)-1-methylpiperidin-3-yl 2-hydroxy-2-phenylacetate;
xl. (S)—(S)-1-methylpiperidin-3-yl 2-hydroxy-2-phenylacetate;
xli. (R)-1-methylpiperidin-4-yl 2-hydroxy-2-phenylacetate;
xlii. (S)-2-hydroxy-N-(1-methylpiperidin-4-yl)-2-phenylacetamide;
xliii. (R)-2-hydroxy-N-(1-methylpiperidin-4-yl)-2-phenylacetamide;
xliv. (R)-2-hydroxy-N—((R)-1-methylpiperidin-3-yl)-2-phenylacetamide;
xlv. (R)-2-hydroxy-N—((S)-1-methylpiperidin-3-yl)-2-phenylacetamide;
xlvi. (S)-2-hydroxy-2-phenyl-N-(pyridin-3-yl)acetamide;
xlvii. (S)-1-methylpiperidin-4-yl 2-hydroxy-2-phenylacetate;
xlviii. (S)-1-benzylazetidin-3-yl 2-hydroxy-2-phenylacetate;
xlix. (S)—(R)-quinuclidin-3-yl 2-hydroxy-2-phenylacetate;
l. (S)—(S)-quinuclidin-3-yl 2-hydroxy-2-phenylacetate;
li. (R)—N-(1-benzylpiperidin-4-yl)-2-hydroxy-2-phenylacetamide;
lii. (S)—N-(1-benzylpiperidin-4-yl)-2-hydroxy-2-phenylacetamide;
liii. (R)-3-((R)-2-hydroxy-2-phenylacetoxy)-1,1-dimethylpiperidin-1-ium;
liv. (S)-3-((R)-2-hydroxy-2-phenylacetoxy)-1,1-dimethylpiperidin-1-ium;
lv. (R)-2-hydroxy-2-phenyl-N-(pyridin-3-yl)acetamide;
lvi. (R)—(S)-1-methylpiperidin-3-yl 2-acetoxy-2-phenylacetate;
lvii. (R)—(R)-1-methylpyrrolidin-3-yl 2-hydroxy-2-phenylacetate;
lviii. (R)—(S)-1-methylpyrrolidin-3-yl 2-hydroxy-2-phenylacetate;
lix. (S)—(R)-1-methylpiperidin-3-yl 2-methoxy-2-phenylacetate;
lx. 2-methoxy-2-phenylacetic acid;
lxi. (R)-2-hydroxy-2-phenyl-N-(piperidin-4-yl)acetamide;
lxii. (R)-piperidin-4-yl 2-hydroxy-2-phenylacetate;
lxiii. (R)-3-(2-hydroxy-2,2-diphenylacetoxy)-1,1-dimethylpiperidin-1-ium;
lxiv. (R)-3-(2-hydroxy-2,2-diphenylacetoxy)-1,1-dimethylpiperidin-1-ium;
lxv. (R)-3-((R)-2-hydroxy-2-phenylacetoxy)-1,1-dimethylpiperidin-1-ium;
lxvi. (R)-3-((R)-2-hydroxy-2-phenylacetoxy)-1,1-dimethylpiperidin-1-ium;
lxvii. (S)—(R)-1-methylpiperidin-3-yl 2-methoxy-2-phenylacetate;
lxviii. (S)—(S)-1-methylpiperidin-3-yl 2-methoxy-2-phenylacetate;
lxix. (S)-2-hydroxy-N—((R)-1-methylpiperidin-3-yl)-2-phenylacetamide;
lxx. (S)-2-hydroxy-N—((S)-1-methylpiperidin-3-yl)-2-phenylacetamide;
lxxi. 3-(2,2-diphenylacetamido)-1,1-dimethylpiperidin-1-ium;
lxxii. (2S)-1-benzyl-2-((2,2-diphenylacetamido)methyl)-1-methylpyrrolidin-1-ium;
lxxiii. 3-(2-hydroxy-2,2-diphenylacetamido)-1,1-dimethylpiperidin-1-ium;
lxxiv. (R)-2-methoxy-1-((S)-3-methylmorpholino)-2-phenylethanone;
lxxv. (R)-2-methoxy-1-((R)-3-methylmorpholino)-2-phenylethanone;
lxxvi. (R)-1-((2R,3S)-2,3-dimethylmorpholino)-2-methoxy-2-phenylethanone;
lxxvii. (S)-2-methoxy-1-((S)-3-methylmorpholino)-2-phenylethanone;
lxxviii. (1R,3R)-1-benzyl-3-(2,2-diphenylacetamido)-1-methylpiperidin-1-ium;
lxxix. (1S,3R)-1-benzyl-3-(2,2-diphenylacetamido)-1-methylpiperidin-1-ium;
lxxx. (1S,3R)-1-benzyl-3-(2,2-diphenylacetamido)-1-methylpiperidin-1-ium;
lxxxi. (1R,3R)-1-benzyl-3-(2,2-diphenylacetamido)-1-methylpiperidin-1-ium;
lxxxii. 1-(3-(benzylamino)piperidin-1-yl)-2,2-diphenylethanone;
lxxxiii. N-((1-benzylpyrrolidin-2-yl)methyl)-2,2-diphenylacetamide;
lxxxiv. 1-benzyl-2-((2,2-diphenylacetamido)methyl)-1-methylpyrrolidin-1-ium;
lxxxv. (R)-2-methoxy-2-phenyl-N-(piperidin-4-yl)acetamide;
lxxxvi. 2-hydroxy-2-phenyl-N-(piperidin-4-yl)acetamide;
lxxxvii. (S)-2-hydroxy-2-phenyl-N-(piperidin-4-yl)acetamide;
lxxxviii. (S)-2-methoxy-2-phenyl-N-(piperidin-4-yl)acetamide;
lxxxix. 2-hydroxy-2-phenyl-N-(piperidin-4-yl)propanamide;
xc. 2-(3-bromo-2,6-difluorophenyl)-2-hydroxy-N-(piperidin-4-yl)acetamide;
xci. (R)-2-methoxy-N-methyl-2-phenyl-N-(piperidin-4-yl)acetamide;
xcii. (R)—N-(1-benzylpiperidin-4-yl)-2-methoxy-N-methyl-2-phenylacetamide;
xciii. (S)-1-benzylpiperidin-4-yl 2-methoxy-2-phenylacetate;
xciv. (R)-ethyl 4-(2-methoxy-2-phenylacetamido)piperidine-1-carboxylate;

B. Salts and Isomers and Counter Ions

The present invention includes within its scope the salts and isomers. Compounds of the present invention after being novel may in some cases form salts which are also within the scope of this invention.

All stereoisomer's of the present compounds, such as those which may exist due to asymmetric carbons on the R substituents of the compound, including enantiomeric and diastereomeric forms, are contemplated within the scope of this invention.

The present invention may also optionally envisage within its scope the effect of selection of suitable counter ions. The present invention includes in its scope, the modification of deuterated compounds. Deuterated compounds are those wherein the compounds have selective incorporation of deuterium in place of hydrogen.

The Compounds of the present invention may be present in their enantiomeric pure forms or their mixtures.

C. Synthesis of the Compounds of the Present Invention

The compounds of the present invention may be synthesized by the any of the synthetic schemes as shown below:

General Synthetic Scheme

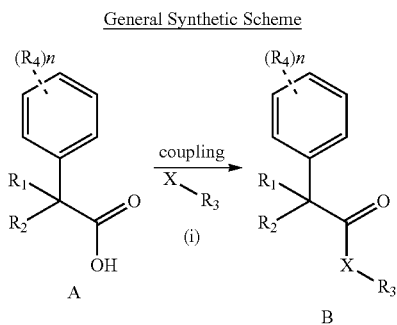

The compounds of present invention may be synthesized by coupling A with B in the presence of (i) as depicted in the scheme above.

X is selected from O, NH or N(alkyl);

$R_1$ and $R_2$ are independently selected from hydrogen, deuterium, hydroxyl, $C_{1-10}$ straight chain or branched chain alkyl, 3-7 membered cycloalkyl, $C_{1-6}$alkoxy, aryl, amino, NH(alkyl), N(alkyl)$_2$, OCOR$_5$, heteroaryl containing 1-3 heteroatoms selected from the group comprising O, N or S; or $R_1$ and $R_2$ may combined to form an aryl or a heteroaryl ring containing 1-3 heteroatoms selected from the group comprising O, N or S;

$R_3$ is selected from hydrogen, hydroxyl, $C_{1-6}$ straight chain or branched chain alkyl, 3-7 membered cycloalkyl, $C_{1-6}$alkoxy, aryl, aromatic or non-aromatic heterocyclic ring or fused heterocyclic ring selected from:

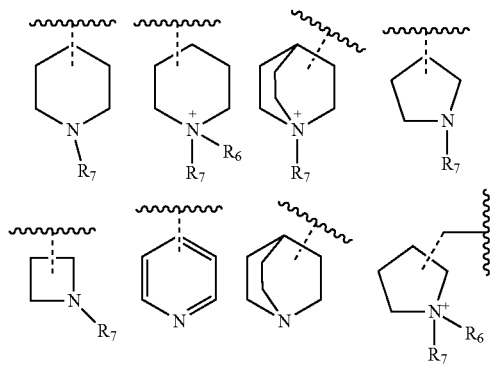

X may in conjunction with R3 form a 5-7 membered heterocyclic ring comprising 1-3 heteroatoms selected from group comprising N, O or S. The heterocyclic ring be further substituted with one or more lower alkyl groups, halogens, amino, NH(alkyl), N(alkyl)2, NH-aralkyl;

R4 is selected from a hydrogen, lower straight chain or branched alkyl, halogen, deuterium, C1-6 alkoxy, amino, NH(alkyl), N(alkyl)2, —COOR8, CONR8R9;

R5 is hydrogen, hydroxy, C1-6alkyl, C1-6alkoxy, amino, NH(alkyl), N(alkyl)2;

R6 and R7 are independently selected from the group comprising hydrogen, C1-10 alkyl, —COR8, —CH2OCOR8, —CH2OCONHR8R9, —COOR8, —CONR8R9, —SO2R8, aryl, aralkyl;

R8 and R9 are independently selected from the group comprising hydrogen, or $C_{1-6}$ straight chain or branched chain alkyl;

n is 1, 2, or 3. and salts, hydrates and stereoisomers thereof.

A general procedure involves the coupling reactions of acid with an amine or alcohol (R$_3$X). In one method, an acid (A) is used as a starting material which can be activated by converting it to corresponding acid chloride using reagent such thionyl chloride or oxalyl chloride in a solvent such as DCM with or without a small amount of DMF at temperature ranging from room temperature to reflux and then by reaction of this acid chloride with a desired amine or alcohol (R$_3$X) to arrive at other members of the series.

Another method involves the use of an acid coupling reagent is such as carbodiimide in an organic solvent such as DMF with or without an organic base such DMAP. Alternatively, acid can be activated by converting to corresponding ester using alcohol such as methanol first before reacting it with an amine or alcohol in a solvent such as benzene with or without a base such as sodium methoxide to arrive at other members of the series.

D. Methods of Use and Pharmaceutical Composition Containing the Novel Entities of the Invention The invention thus provides the use of the novel compounds as defined herein for use in human or veterinary medicine. The compounds of the present invention may be used in the treatment and prevention of diseases caused by mycobacteria such as tuberculosis. The said tuberculosis may be caused by mycobacterial species consisting of *Mycobacterium tuberculosis, M. bovis, M africanum, M. canettior M. microti*. Particularly, the compounds of the present invention are effective in inhibiting the growth of the *M. tuberculosis*. Tuberculosis as mentioned herein comprises active tuberculosis or latent tuberculosis. The active tuberculosis comprises drug sensitive, mono-drug resistant, multi-drug-resistant tuberculosis (MDR), extensively drug-resistant tuberculosis (XDR) or totally drug resistant tuberculosis.

In an aspect, the compounds of the present invention may be used in the treatment of tuberculosis including MDR, XDR and TDR tuberculosis.

In an aspect, the compounds of the present invention may be used either alone or in combination with cycloserine, amikacin, linezolid, ethambutol, rifampicin, isoniazid, ethionamide, moxyfloxacin, clarithromycin, PAS, clofazamine, streptomycin, capreomycin and kanamycin and DOTS ("Directly Observed Treatment, Short-course") therapy.

In another aspect, the compounds of the present invention may also be used prophylactically in preventing the occurrence of tuberculosis in healthcare providers, health workers, community members and the alike who are directly in contact with tuberculosis patients.

The compounds of the present invention may be used for treatment of the infection caused by resistant and non-resistant *Mycobacterium tuberculosis* as defined above. The compounds of the present invention are effective against tuberculosis and said tuberculosis includes drug-sensitive, mono-drug resistance, multi drug-resistant (MDR), extensively drug-resistance (XDR) and totally drug resistance (TDR) caused by a strain of *Mycobacterium tuberculosis*

Mycobacterium strains. The compounds of the present invention may be used for the treatment of multi-drug-resistant (MDR), extensively drug-resistance (XDR) and totally drug resistance (TDR) tuberculosis caused by a strain *Mycobacterium tuberculosis* and for treatment of the infection caused by resistant and non-resistant *Mycobacterium tuberculosis* as defined above by inhibition of GPR109A inhibition by an agent.

The compound for use as a pharmaceutical may be presented as a pharmaceutical composition. The invention therefore provides in a further aspect a pharmaceutical composition comprising the novel compounds of the invention along with pharmaceutically acceptable excipients/carriers thereof and optionally other therapeutic and/or prophylactic ingredients. The excipients/carriers must be "acceptable" in the sense of being compatible with the other ingredients of the composition and not deleterious to the recipient thereof. Suitably the pharmaceutical composition will be in an appropriate formulation.

The pharmaceutical formulations may be any formulation and include those suitable for oral, intranasal, or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation.

For these purposes the compounds of the present invention may be administered orally, topically, intranasally, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasteral injection or infusion techniques. In addition to the treatment of warm-blooded animals such as mice, rats, horses, dogs, cats, etc. The compounds of the present invention are effective in the treatment of humans.

In an aspect, compound of the present invention may be administered in a dose ranging from 0.1 to 100 mg/kg body weight per day. The compounds of the present invention are useful for the prevention and treatment of tuberculosis and may be used as GPR109A inhibitors.

E. Experimentals

The compounds of present invention may be prepared by the schemes as here below:

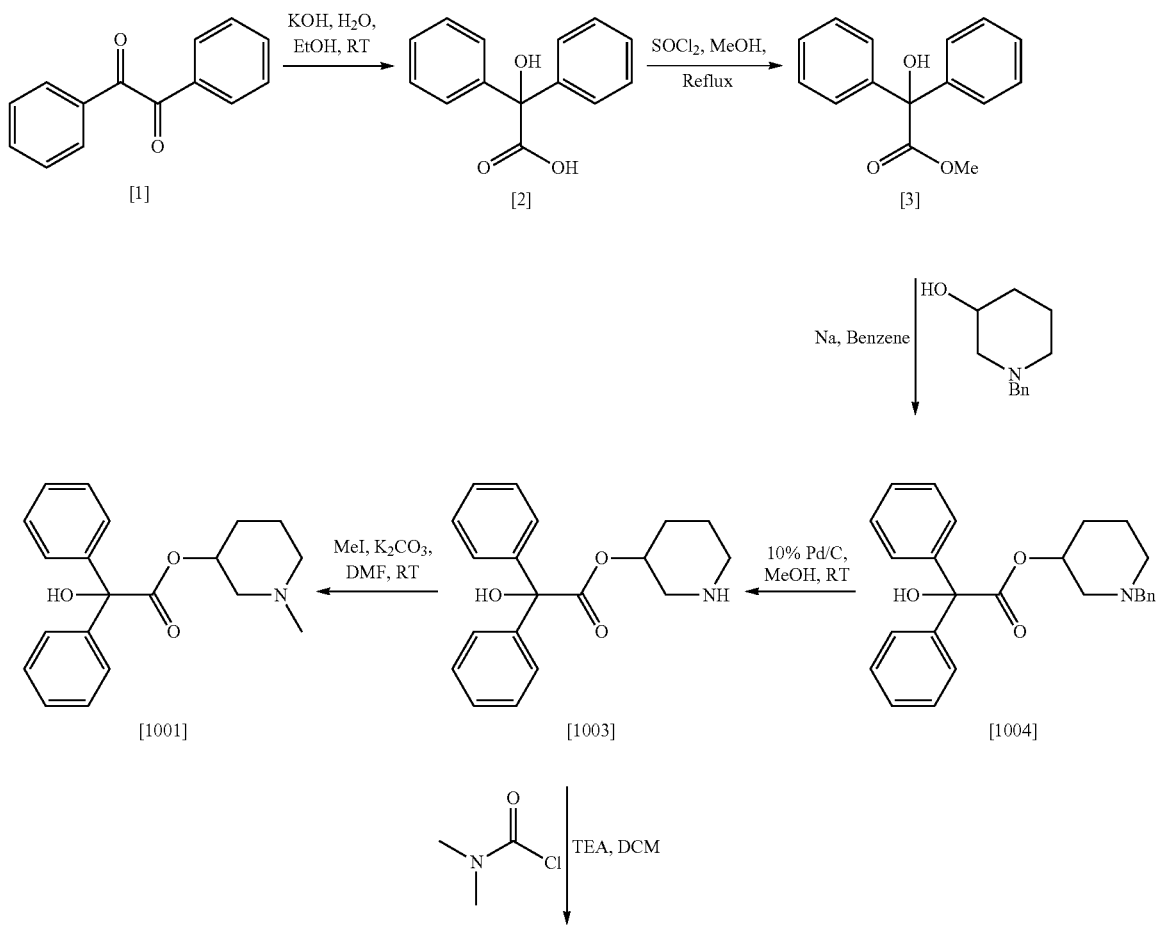

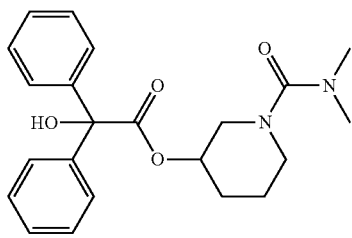

[1006]

Step 1:

To a solution of KOH (21.0 gm) in water (42.0 ml), ethanol (54.0 ml) and the compound [1](25.0 g, 119 mmol) was added and the resulting solution was refluxed for 30 minutes and poured into a glass plate and left overnight at RT. The semisolid obtained was dissolved in water (400 ml) and washed with ethyl acetate. The pH of the aqueous layer was adjusted to acidic with 50% HCl, and extracted with ethyl acetate. The ethyl acetate layer was dried over anhydrous $Na_2SO_4$ and concentrated to give 2-hydroxy-2,2-diphenylacetic acid, (12.0 g, 45%). Analytical Data: [2] ESIMS: 229 [M$^+$+1]

Step 2

To a solution of the compound obtained in the above step (12 g, 52.6 mmol) in Methanol (100.0 ml) at 0° C., thionyl chloride (5.0 ml) was added and the resulting solution was refluxed for 4 hr. Ethanol was concentrated under vacuum and the residue was purified by column chromatography using 20% ethyl acetate in hexane to give ethyl 2-hydroxy-2,2-diphenylacetate as liquid (10.08 g, 76%). Analytical Data: [3] ESIMS: 257 [M$^+$+1]

Step 3:

To a solution of [3] (1.00 g, 5.23 mmol) in benzene (90 mL), sodium (110 mg) was added. After refluxing for 2.5 h, a solution of methylbenzilate (1.27 g, 5.23 mmol) was added and the reaction refluxed overnight. The benzene was evaporated in vacuo and the residue purified by flash chromatography (eluted first with 20% EtOAc/Hexane, then 5% MeOH/$CH_2Cl_2$) to give [1004] as transparent liquid (981 mg, 46%). Analytical Data: [1004] ESIMS: 402[M$^+$+1]

Step 4:

To a stirred solution of [1004] (0.5 g, 1.24 mmol) in a mixture of ethyl acetate and methanol (1;1, 5 ml), was added a slurry of 10% Pd/C (0.02 g) at room temperature. Hydrogen balloon pressure was applied and the reaction mixture was stirred for 3 hr at RT. Reaction was monitored using TLC. The reaction mass was filtered over celite and excess of solvent was removed under vacuum to afford light brown sticky material, which was further purified using silica gel column and 2% methanol in dichloromethane as eluent to afford [1003] as an off-white sticky material (0.22 g, 57%). Analytical Data: [1003] ESIMS: 312 [M$^+$+1]

Step 5:

To a stirred solution of [1003] (0.12 g, 0.38 mmol) in DMF, anhydrous $K_2CO_3$ (0.05 g, 0.41 mmol) was added at 0° C. under nitrogen atmosphere. After an additional stirring for 15 minutes at same temperature, Methyl iodide (0.02 ml, 0.41 mmol) was added drop-wise. The reaction temperature was allowed to increase up to 25° C. and stirring was continued for 3 h. Consumption of [1003] was monitored by TLC. After complete consumption of [1003], water (50 ml) was added and organic layer was extracted with ethyl acetate (2×50 ml). The combined organic layers were washed with water, brine and dried over sodium sulphate. The organic layer was concentrated to afford light brown sticky material which was further purified using silica gel column chromatography using 5% ethyl acetate/hexane as eluent to afford [1001] as white solid (0.08 g, 65%,). Analytical Data: [1001] ESIMS: 326 [M$^+$+1].

Step 6:

To a stirred solution of [1003] (0.05 g, 0.16 mmol) in DCM, triethylamine (0.03 ml, 0.24 mmol) was added at 0° C. under nitrogen atmosphere. After an additional stirring for 5 minutes at same temperature, Dimethylcarbamoyl chloride (0.02 ml, 0.24 mmol) was added drop-wise. The reaction temperature was allowed to increase up to 25° C. and stirring was continued for 1 h. Consumption of [1003] was monitored by TLC. After complete consumption of [1003], water (50 ml) was added and organic layer was extracted with ethyl acetate (2×25 ml). The combined organic layers were washed with water, brine and dried over sodium sulphate. The organic layer was concentrated to afford light brown sticky material which was washed further with DCM and pentane to afford [1006] (0.04 g, 65%). Analytical Data: [1006] ESIMS: 385 [M$^+$+1].

Synthesis of [1010], [1012], [1008], [1013], [1018], [1007], [1009], [1014], [1019] and [1023] were carried out by procedure described for [1004].

Synthesis of [1005], [1011] and [1015] were carried out by procedure described for [1006].

Synthetic Scheme 2:

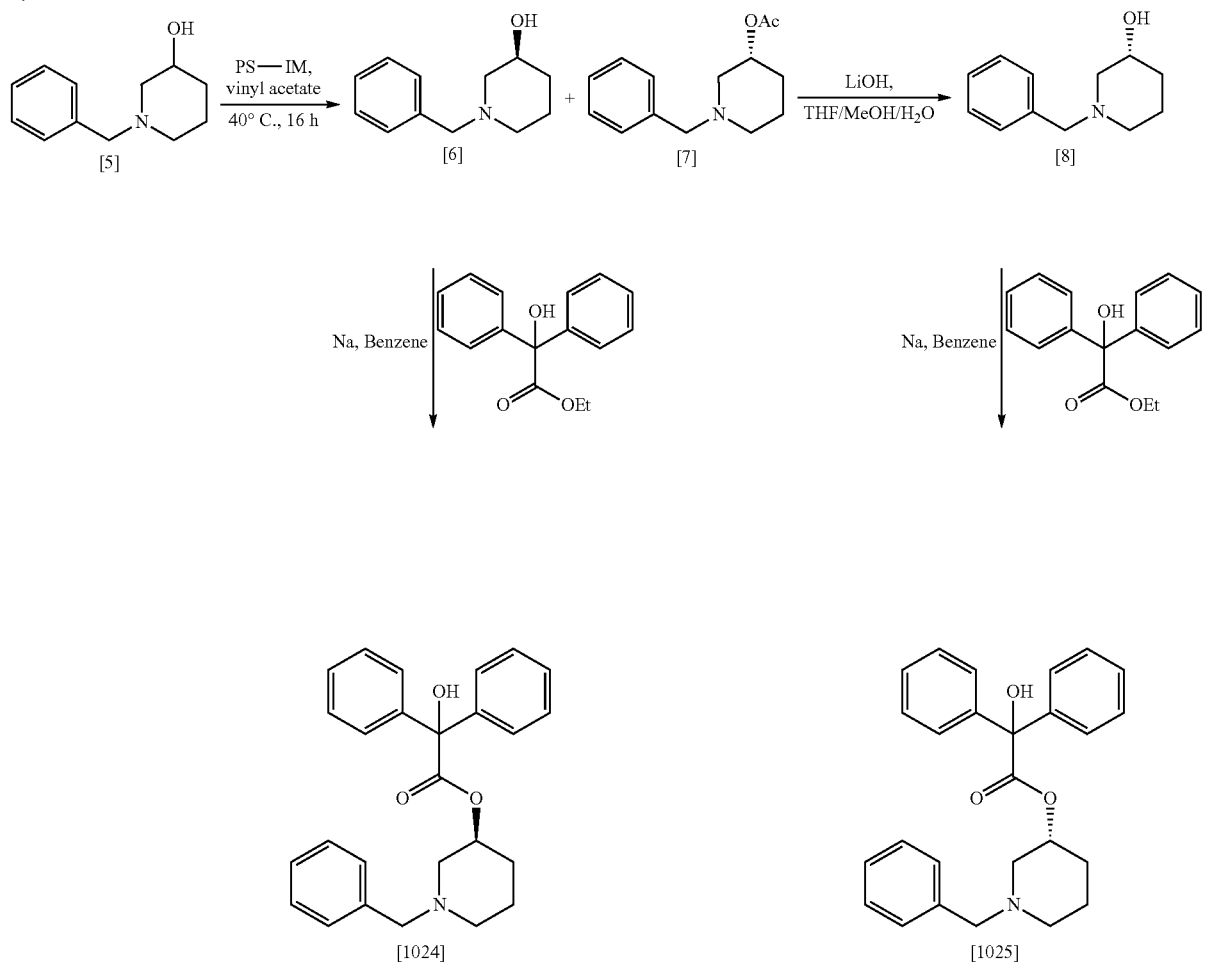

Step 1:

To a stirred solution of [5] (2.0 g, 10.47 mmol), vinyl acetate (10.0 ml, 100.0 mmol) was added at room temperature. After an additional stirring for 5 minutes at same temperature, PS-IM (0.20 g, 10%) was added. The reaction temperature was allowed to increase up to 40° C. and stirring was continued for 16 h. Reaction mixture was passed through the bed of celite and evaporated to dryness which was further purified using silica gel column chromatography using 10% ethyl acetate/hexane as eluent to afford [6] (0.9 g, 45%) and [7] (0.8 g, 40%) as transparent sticky material. Analytical Data: [6] ESIMS: 192 [M$^+$+1][7] ESIMS: 234 [M$^+$+1].

Step 2:

To a solution of [6] (0.45 g, 1.8 mmol) in benzene (45 mL) was added sodium (0.03 g, 1.6 mmol). After refluxing for 2.5 h, a solution of ethyl benzilate (0.35 g, 1.8 mmol) was added and the reaction refluxed overnight. The benzene was evaporated in vacuo and the residue purified by flash chromatography (eluted first with 20% EtOAc/Hexane, then 5% MeOH/CH$_2$Cl$_2$) to give [1024] as transparent liquid (0.35 g, 48%).

Analytical Data: [1024] ESIMS: 402[M$^+$+1]

Step 3:

To a solution of [7] (0.60 g, 2.5 mmol) in a mixture of THF/MeOH/H$_2$O (9 ml) was added Lithium hydroxide (0.20 g, 5.0 mmol). The reaction mixture was stirred at room temperature for 4 h. TLC showed complete consumption of starting material. Reaction mixture was evaporated to dryness. Water was added and extracted with ethylacetate (2×50 ml) to afford light transparent sticky material [8] (0.35 g, 73%). Analytical Data: [8] ESIMS: 192[M$^+$+1]

Step 4:

[1025] was synthesized as described in step 2. Analytical Data: [1025] ESIMS: 402[M$^+$+1] Synthesis of [1026] and [1027] were carried out by procedure described for [1024]

Synthetic Scheme 3:

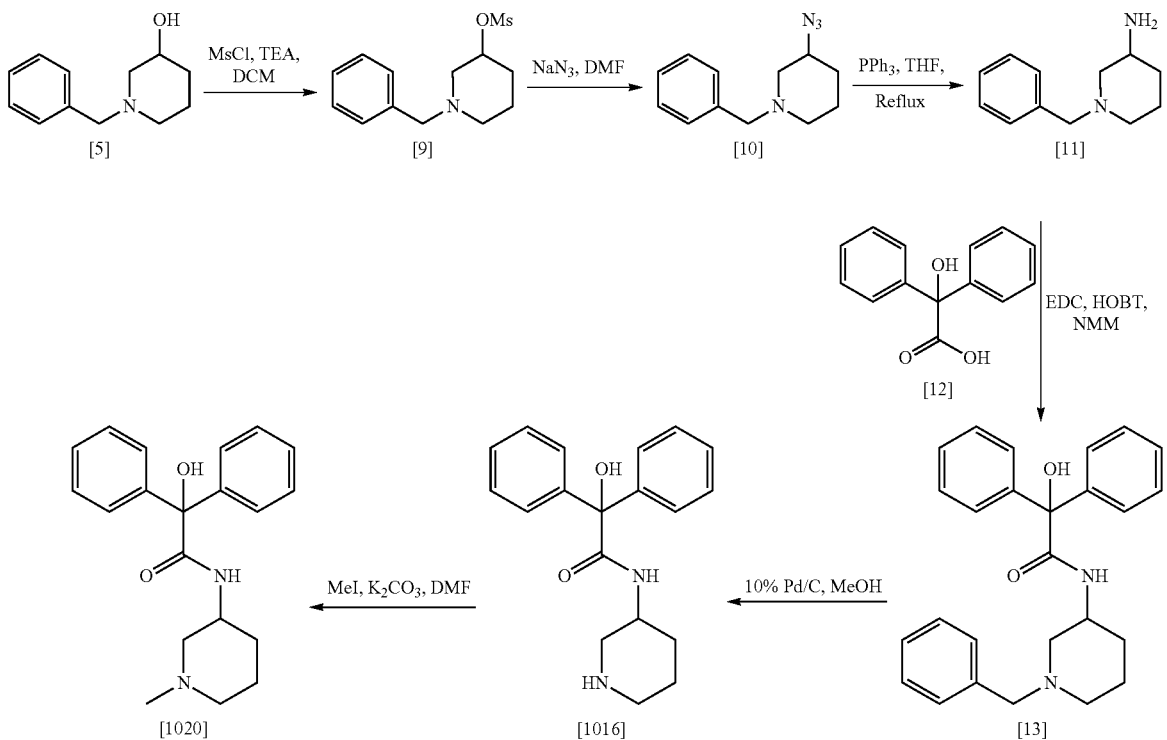

Step 1:
To a stirred solution of [5] (1.0 g, 5.2 mmol) in DCM (20.0 ml) was added TEA (1.9 g, 15.2 mmol) at room temperature. After an additional stirring for 5 minutes at same temperature, Mesyl chloride (0.55 ml, 7.8 mmol) was added. The reaction temperature was allowed to stirred at this temperature for 3 h. TLC showed complete consumption of starting material. Water (100 ml) was added and organic layer was extracted with ethyl acetate (2×100 ml). The combined organic layers were washed with water, brine and dried over sodium sulphate. The organic layer was concentrated to afford light brown sticky material [9] which was used further without any purification (1.1 g, 78%). Analytical Data: [9] ESIMS: 270 [M$^+$+1].

Step 2:
To a stirred solution of [9] (0.5 g, 1.8 mmol) in DMF (10.0 ml) was added sodium azide (0.46 g, 7.2 mmol) at room temperature. The temperature of reaction mixture was raised to 100° C. and allowed to heat at this temperature for 2 hr. TLC showed complete consumption of starting material. Water (100 ml) was added and organic layer was extracted with ethyl acetate (2×100 ml). The combined organic layers were washed with water, brine and dried over sodium sulphate. The organic layer was concentrated to afford light brown sticky material [10] which was used further without any purification (0.3 g, 77%). Analytical Data: [10] ESIMS: 217 [M$^+$+1].

Step 3:
To a stirred solution of [10] (0.3 g, 1.3 mmol) in THF (10.0 ml) was added triphenylphosphine (0.5 g, 1.9 mmol) at room temperature. After an additional stirring for 5 minutes at same temperature, water (0.2 ml, 9.1 mmol) was added. The reaction temperature was allowed to reflux at 70° C. for 2 h. TLC showed complete consumption of starting material. Reaction mixture was evaporated and water (100 ml) was added and organic layer was extracted with ethyl acetate (2×100 ml). The combined organic layers were washed with water, brine and dried over sodium sulphate. The organic layer was concentrated to afford light brown sticky which was subjected to column chromatography with 2% MeOH/DCM as eluent to afford light brown sticky material [11] (0.2 g, 80%). Analytical Data: [11] ESIMS: 191 [M$^+$+1]

Step 4:
To a stirred solution of [12] (0.2 g, 0.87 mmol) in DMF (5.0 ml) was added EDC (0.25 g, 1.3 mmol), HOBT (0.17 g, 1.3 mmol) at room temperature. After an additional stirring for 5 minutes at same temperature, [11] (0.18 g, 0.91 mmol) and NMM (0.37 ml, 2.61 mmol) was added. The reaction temperature was allowed to stirred at room temperature for overnight. TLC showed complete consumption of starting material. Water (100 ml) was added and organic layer was extracted with ethyl acetate (2×100 ml). The combined organic layers were washed with water, brine and dried over sodium sulphate. The organic layer was concentrated to afford light brown sticky which was subjected to column chromatography with 1% MeOH/DCM as eluent to afford light brown solid material [13] (0.25 g, 76%). Analytical Data: [13] ESIMS: 400 [M$^+$+1]

Step 5:
To a stirred solution of [13] (0.25 g, 0.62 mmol) in a mixture of ethyl acetate and methanol (1;1, 5 ml), was added a slurry of 10% Pd/C (0.02 g) at room temperature. Hydrogen balloon pressure was applied and the reaction mixture was stirred for 3 hr at RT. Reaction was monitored using TLC. The reaction mass was filtered over celite and excess of solvent was removed under vacuum to afford light brown sticky material, which was further purified using silica gel column and 2% methanol in dichloromethane as eluent to afford [1016] as off white sticky material (0.11 g, 57%). Analytical Data: [1016] ESIMS: 311 [M⁺+1]

Step 6:

To a stirred solution of [1016] (0.10 g, 0.32 mmol) in DMF, anhydrous K₂CO₃ (0.06 g, 0.48 mmol) was added at 0° C. under nitrogen atmosphere. After an additional stirring for 15 minutes at same temperature, Methyl iodide (0.03 ml, 0.48 mmol) was added drop-wise. The reaction temperature was allowed to increase up to 25° C. and stirring was continued for 3 h. Consumption of [1016] was monitored by TLC. After complete consumption of [1016], water (50 ml) was added and organic layer was extracted with ethyl acetate (2×50 ml). The combined organic layers were washed with water, brine and dried over sodium sulphate. The organic layer was concentrated to afford light brown sticky material which was further purified using silica gel column chromatography using 10% ethyl acetate/hexane as eluent to afford [1020] as white solid (0.05 g, 50%,). Analytical Data: [1020] ESIMS: 325 [M⁺+1] Synthesis of [1017], [1021], [1022], [1028], [1029], [1030], [1031] and [1032] were carried out by procedure described for [1020]

HPLC to afford [1037] (0.10 g, 9%) and [1038](0.08 g, 8%) as transparent sticky material. Analytical Data: [1037 and 1038] ESIMS: 250 [M⁺+1].

Step 2:

To a stirred solution of [1037] (0.05 g, 0.20 mmol) in Acetonitrile (2 ml), methyl iodide (0.01 ml, 0.20 mmol) was added at room temperature under nitrogen atmosphere. The reaction temperature was allowed to stirred at this temperature for overnight. After complete consumption of [1037], reaction mixture was evaporated to dryness to afford light yellow solid which was further purified by washing with Dichloromethane and ether to afford pure product [1065] (0.04 g, 51%). Analytical Data: [1065] ESIMS: 364 [M⁺]. Step 3 [1064] was synthesized similar to [1065] as described in step 2. Analytical Data: [1064] ESIMS: 364[M⁺]

Synthesis of [1039], [1040], [1041], [1042], [1043], [1044], [1045], [1046], [1047], [1048], [1049], [1050], [1051], [1052], [1055], [1057], [1058], [1059], [1053], [1054], [1063], [1067], [1068], [1069], [1070], [1071], [1073], [1061], [1062], [1074], [1075], [1076], [1077] and [1093] were carried out by procedure described for [1064] and [1065].

Synthetic Scheme 4:

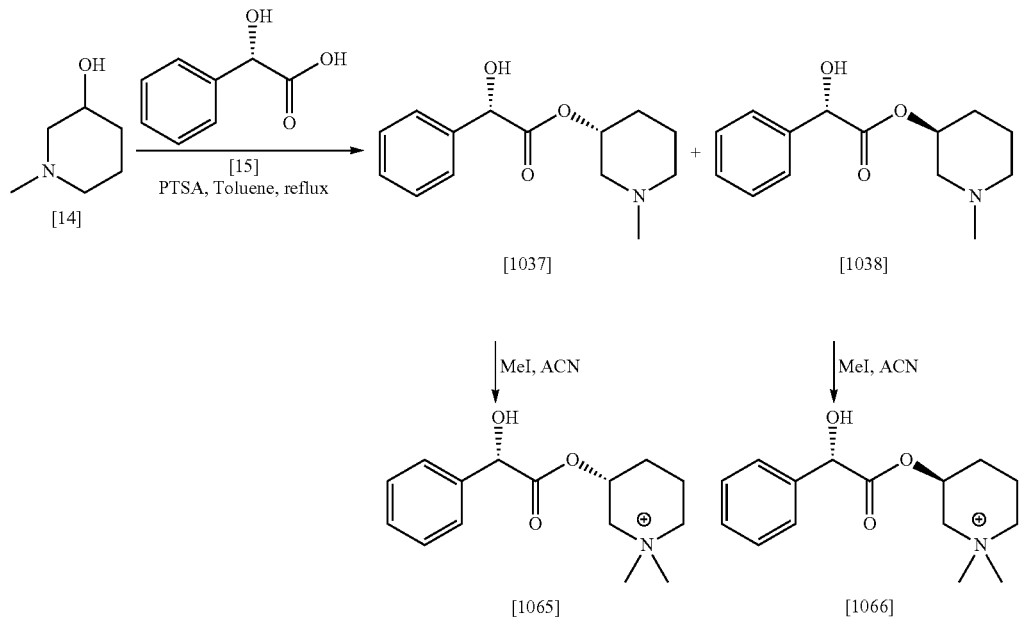

Step 1:

To a stirred solution of [14] (0.50 g, 4.34 mmol) in benzene (30 ml), PTSA (0.74 g, 4.34 mmol) was added at room temperature under nitrogen atmosphere. After an additional stirring for 15 minutes at same temperature, [15] (0.65 g, 4.34 mmol) was added. The reaction temperature was allowed to increase up to 90° C. and stirring was continued for 5 h. Consumption of [15] was monitored by TLC. After complete consumption of [15], water (50 ml) was added and organic layer was extracted with ethyl acetate (3×50 ml). The combined organic layers were washed with water, brine and dried over sodium sulphate. The organic layer was concentrated to afford light brown sticky material which was further purified using silica gel column chromatography using 30% ethyl acetate/hexane as eluent to afford mixture of [1037] and [1038] which was further separated by prep- Synthetic Scheme 5:

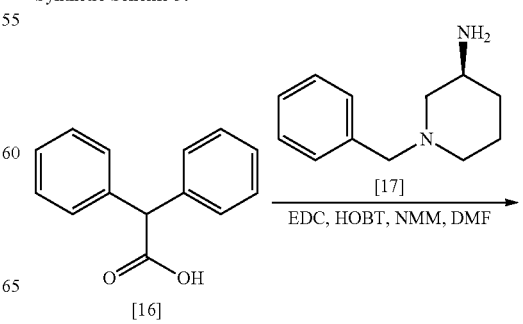

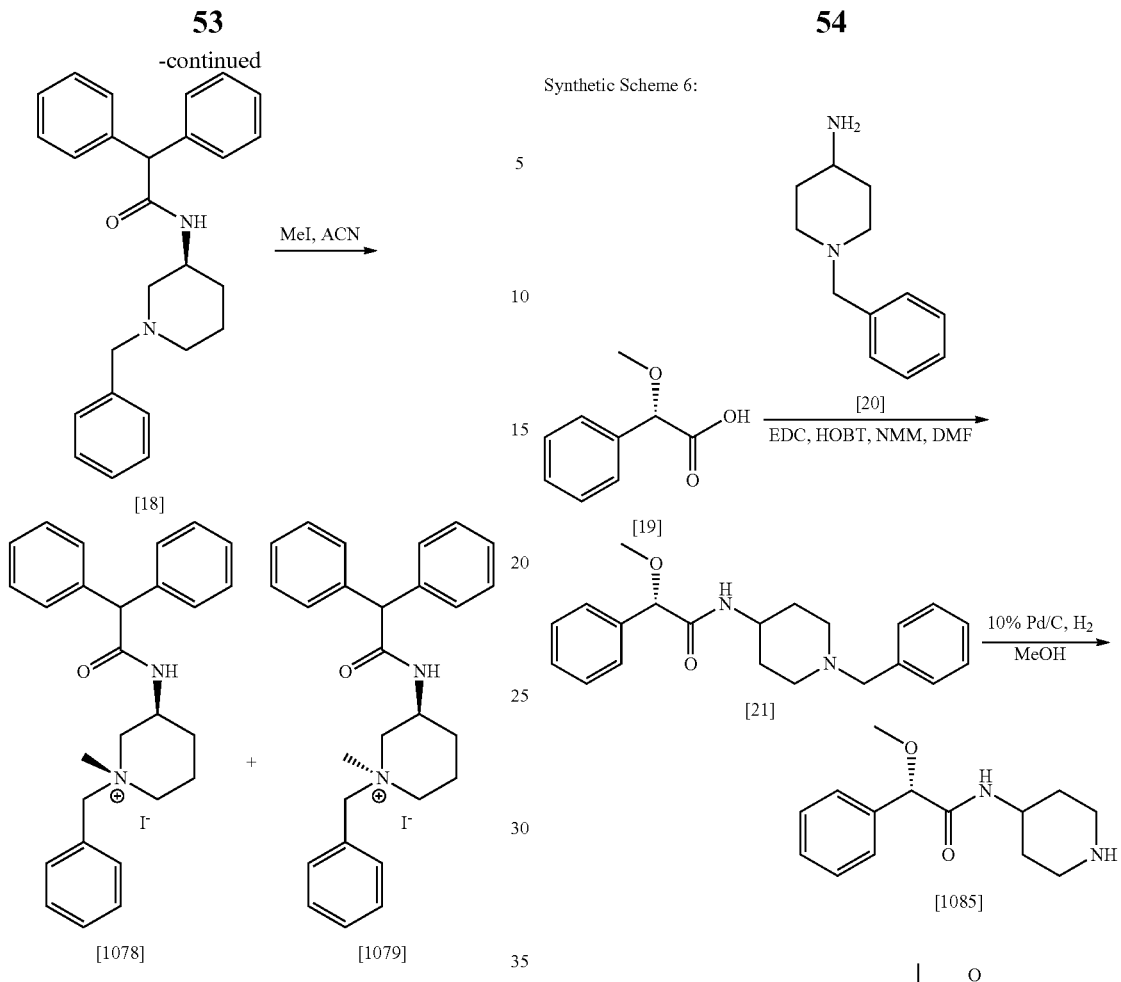

Step 1:

To a stirred solution of [17] (0.08 g, 0.42 mmol) in DMF (5.0 ml) was added EDC (0.12 g, 0.63 mmol), HOBT (0.08 g, 0.63 mmol) at room temperature. After an additional stirring for 5 minutes at same temperature, [16] (0.08 g, 0.42 mmol) and NMM (0.14 ml, 2.3 mmol) was added. The reaction temperature was allowed to stir at room temperature for overnight. TLC showed complete consumption of starting material. Water (100 ml) was added and organic layer was extracted with ethyl acetate (2×100 ml). The combined organic layers were washed with water, brine and dried over sodium sulphate. The organic layer was concentrated to afford light brown sticky which was subjected to column chromatography with 1% MeOH/DCM as eluent to afford off white solid material [18] (0.11 g, 68%). Analytical Data: [18] ESIMS: 385 [M$^+$+1].

Step 2:

To a stirred solution of [18] (0.11 g, 0.28 mmol) in Acetonitrile (2 ml), methyl iodide (0.02 ml, 0.28 mmol) was added at room temperature under nitrogen atmosphere. The reaction temperature was allowed to stirred at this temperature for overnight. After complete consumption of [18], reaction mixture was evaporated to dryness to afford light yellow solid as a mixture of [11081] and [11082] which was further purified by prep-HPLC to afford [1078] (0.03 g, 20%) and [1079] (0.4 g, 27%) as light yellow solid material. Analytical Data: [1078 and 1079] ESIMS: 399 [M$^+$].

Synthesis of [1080], [1081], [1082], [1083], [1084] and [1034] were carried out by procedure described for [1078] and [1079]

Step 1:

To a stirred solution of [19] (0.80 g, 4.81 mmol) in DMF (5.0 ml) was added EDC (1.40 g, 7.2 mmol), HOBT (0.97 g, 7.2 mmol) at room temperature. After an additional stirring for 5 minutes at same temperature, [20] (1.11 ml, 5.30 mmol) and NMM (1.6 ml, 14.43 mmol) was added. The reaction temperature was allowed to stirred at room temperature for overnight. TLC showed complete consumption of starting material. Water (100 ml) was added and organic layer was extracted with ethyl acetate (2×100 ml). The combined organic layers were washed with water, brine and dried over sodium sulphate. The organic layer was concentrated to afford light yellow powder which was triturated with pentane to afford off white solid material [21] (1.20 g, 75%). Analytical Data: [21] ESIMS: 339 [M$^+$+1].

Step 2:

To a stirred solution of [21] (0.5 g, 1.4 mmol) in methanol (10 ml), was added a slurry of 10% Pd/C (0.05 g) at room temperature. Hydrogen balloon pressure was applied and the reaction mixture was stirred for 3 hr at RT. Reaction was monitored using TLC. The reaction mass was filtered over celite and excess of solvent was removed under vacuum to afford off white powder [1085] (0.3 g, 86%). Analytical Data: [1085] ESIMS: 249 [M$^+$+1].

Step 3:

To a stirred solution of [1085 Hydrochloride] (0.05 g, 0.20 mmol) in DCM, triethylamine (0.07 ml, 0.5 mmol) was added at 0° C. under nitrogen atmosphere. After an additional stirring for 5 minutes at same temperature, Ethyl chloroformate (0.02 ml, 0.22 mmol) was added drop-wise. The reaction temperature was allowed to increase up to 25° C. and stirring was continued for 1 h. Consumption of [1085] was monitored by TLC. After complete consumption of [1085], water (50 ml) was added and organic layer was extracted with ethyl acetate (2×25 ml). The combined organic layers were washed with water, brine and dried over sodium sulphate. The organic layer was concentrated to afford light brown sticky material which was washed further with DCM and pentane to afford [1094] (0.03 g, 64%). Analytical Data: [1094] ESIMS: 321 [M$^+$+1].

Synthesis of [1086], [1087], [1088], [1089], [1090], [1091], [1092], [1035] and [1036] were carried out by procedure described for [1085].

F. Biological Testing of the Compounds of Present Invention

EXAMPLE 1

Inhibition of *Mycobacterium* Colony Growth in Macrophage by Compounds of the Present Invention THP1 cells were seeded in a tissue culture plate in complete RPMI+10% FCS and were allowed to differentiate to macrophages by addition of PMA with incubation at 37° C. with 5% $CO_2$. After 16-20 hr of PMA differentiation, cells were washed and replenished with complete RPMI. PMA-differentiated THP-1 cell were infected with tuberculosis bacteria H37Rv at an MOI of 10. Infection was performed in antibiotic free RPMI supplemented with 10% FCS. After adding bacteria, culture plates were centrifuged prior to incubation at 37° C. with 5% $CO_2$. After 4 hr, infected cells were washed twice with warm RPMI and replenished with complete RPMI containing Amikacin to remove any remaining extra-cellular bacteria. Compound was added at concentrations of 5 to 500 nM at 16 hr and medium containing the appropriate dose of compound was refreshed every 24 hr up to the 64 hr time point. At the end of the assay at 90 hr, cells were lysed with lysis buffer (7H9+0.06% SDS) and the residual bacterial loads determined as CFU counts. The results are graphically depicted in Table 2 which demonstrates that growth of Mycobacterial colony stood inhibited upon use of these compounds.

TABLE 2

Screening of compounds for H37Rv % inhibition at 100 nM and 500 nM

| Compound No. | H37Rv % Inhibition at 500 nM |
|---|---|
| 1001 | 73 |
| 1002 | NT |
| 1003 | 22 |
| 1004 | 33 |
| 1005 | 55 |
| 1006 | 66 |
| 1007 | 46 |
| 1008 | 42 |
| 1009 | 46 |
| 1010 | 46 |
| 1011 | 51 |
| 1012 | 51 |
| 1013 | 55 |
| 1014 | 77 |
| 1015 | 73 |
| 1016 | 65 |
| 1017 | 75 |
| 1018 | 66 |
| 1019 | 60 |
| 1020 | 64 |
| 1021 | 74 |
| 1022 | 75 |
| 1023 | 50 |
| 1024 | 72 |
| 1025 | 79 |
| 1026 | 71 |
| 1027 | 85 |
| 1028 | 77 |
| 1029 | 61 |
| 1030 | 52 |
| 1031 | 74 |
| 1032 | 72 |
| 1033 | 78 |
| 1034 | 64 |
| 1035 | 62 |
| 1036 | 58 |
| 1037 | 40 |
| 1038 | 56 |
| 1039 | 61 |
| 1040 | 79 |
| 1041 | 71 |
| 1042 | 73 |
| 1043 | 72 |
| 1044 | 65 |
| 1045 | 66 |
| 1046 | 56 |
| 1047 | 68 |
| 1048 | 79 |
| 1049 | 56 |
| 1050 | 42 |
| 1051 | 59 |
| 1052 | 73 |
| 1053 | 78 |
| 1054 | 74 |
| 1055 | 52 |
| 1056 | 78 |
| 1057 | 76 |
| 1058 | 55 |
| 1059 | 74 |
| 1060 | 78 |
| 1061 | NT |
| 1062 | NT |
| 1063 | NT |
| 1064 | NT |
| 1065 | NT |
| 1066 | NT |
| 1067 | NT |
| 1068 | NT |
| 1069 | NT |
| 1070 | NT |
| 1071 | NT |
| 1072 | NT |
| 1073 | NT |
| 1074 | 24 |
| 1075 | 46 |
| 1076 | 50 |
| 1077 | 52 |
| 1085 | 93 |

NT = Not Tested

EXAMPLE 3

In Vitro Infection of Human PBMC Derived Macrophages, Compound Addition and Cfu Determination Heparinised human blood diluted 1:1 with RPMI 1640 was layered onto equal volume of Ficoll-Paque followed by centrifugation at 1600 rpm for 30 min. The PBMC layer formed at the interface was collected carefully and washed twice with RPMI. The cells were diluted in RMPI medium (without serum) to a concentration $2\times10^6$/ml and 10 ml of diluted cells were put into a 75-cm² tissue culture flask, and incubated for 2 hrs in a humidified 37° C. incubator. The non-adherent cells were removed by aspiration, followed by two washes with RPMI. Complete media (with 10% FCS) was added and the cells were allowed to spontaneously differentiate into macrophages for 4 days in a humidified 37° C., 5% $CO_2$ incubator. Bacteria were grown in Middlebrooke 7H9 broth supplemented with 10% ADC, 0.4% Glycerol and 0.05% Tween-80 until the mid-log phase. The bacteria were then harvested, washed with RPMI and re-suspended in the same media. The suspension was dispersed by aspiration twelve times each with a 23- and then a 26-gauge needle, followed by an additional dispersion for 3 times through a 30-gauge needle. This suspension was allowed to stand for 5 min. The upper half of the suspension was then used for the experiments. Bacteria were quantified by measuring the absorbance at a wavelength 600 nm (0.6 O.D. corresponds to $\sim100\times10^6$ bacteria).

Human PBMC derived macrophages were infected with tuberculosis bacteria at a MOI of 10 (i.e., 10 bacteria per cell). Infection was performed in antibiotic free RPMI supplemented with 10% FCS. After adding bacteria, culture plates were centrifuged at 700 rpm for 5 min prior to incubation at 37° C. with 5% $CO_2$. After 4 h, infected cells were washed twice with warm RPMI and replenished with complete RPMI containing 200 μg/mL amikacin for 2 h to remove any remaining extra-cellular bacteria. Subsequently, cells were washed and then maintained in complete RPMI for the rest of the experiment. Inhibitor addition was performed at 16 hrs post infection (p.i) and the medium containing the appropriate dose of inhibitor was replenished at 40 hrs and 64 hrs p.i. At 90 h post infection, the cells were lysed in 50 μl of 0.06% SDS for 10 min at room temperature. Lysate dilutions of 1:10 were plated in duplicate sets on 7H11 agar plates. Square plates (12×12 cm) were used for the plating, by the track dilution method in which 10 μl of each dilution was spotted on one side of square plate. The plate was then tipped onto its side (at a 45°-90° angle), and the spots were allowed to gently flow in parallel tracks along the agar surface. The plates were then allowed to dry and subsequently incubated in a humidified incubator at 37° C. Colonies were counted on the 14th day and converted into cfu/well. The effect of one of the compounds of the present invention in reducing mycobacterial growth in human PBMC derived macrophages is shown as means of illustration at Table 3.

TABLE 3

Demonstration of reduction of colony count on use of the compound 1085

| | CFU/well ($1 \times 10^3$) of untreated cells | CFU/well ($1 \times 10^3$) After treatment with 1085 |
| --- | --- | --- |
| JAL2287 | 42.00 ± 2.00 | 6.33 ± 3.51 |
| MYC431 | 20.67 ± 1.53 | 6.00 ± 1.00 |
| H37RV | 27.67 ± 2.08 | 8.66 ± 2.51 |

EXAMPLE 4

In Vitro Infection of THP-1 Macrophages, Compound Addition and Cfu Determination The human monocyte/macrophage cell line THP-1 was cultured in RPMI 1640 supplemented with 10% FCS and were maintained between 2 and $10\times10^5$ cells per ml at 37° C. in a humidified, 5% $CO_2$ atmosphere. Before infection, cells were plated in 96 well plates at $1\times10^4$ cells per well and differentiated with PMA (30 ng/ml) for a period of 48 hrs. Bacteria were grown in Middlebrooke 7H9 broth supplemented with 10% ADC, 0.4% Glycerol and 0.05% Tween 80 until the mid-log phase. The bacteria were then harvested, washed with RPMI and re-suspended in the same media. The suspension was dispersed by aspiration twelve times each with a 23- and then a 26-gauge needle, followed by an additional dispersion for 3 times through a 30-gauge needle. This suspension was allowed to stand for 5 min. The upper half of the suspension was then used for the experiments. Bacteria were quantified by measuring the absorbance at a wavelength 600 nm (0.6 O.D. corresponds to $\sim100\times10^6$ bacteria).

PMA-differentiated THP-1 cells were infected with tuberculosis bacteria at a MOI of 10 (i.e., 10 bacteria per cell). Infection was performed in antibiotic free RPMI supplemented with 10% FCS. After adding bacteria, culture plates were centrifuged at 700 rpm for 5 min prior to incubation at 37° C. with 5% $CO_2$. After 4 h, infected cells were washed twice with warm RPMI and replenished with complete RPMI containing 200 μg/mL amikacin for 2 h to remove any remaining extra-cellular bacteria. Subsequently, cells were washed and then maintained in complete RPMI for the rest of the experiment. Inhibitor addition was performed at 16 hrs post infection (p.i) and the medium containing the appropriate dose of inhibitor was replenished at 40 hrs and 64 hrs p.i. At 90 h post infection, the cells were lysed in 50 μl of 0.06% SDS for 10 min at room temperature. Lysate dilutions of 1:10 were plated in duplicate sets on 7H11 agar plates. Square plates (12×12 cm) were used for the plating, by the track dilution method in which 10 μl of each dilution was spotted on one side of square plate. The plate was then tipped onto its side (at a 450-90° angle), and the spots were allowed to gently flow in parallel tracks along the agar surface. The plates were then allowed to dry and subsequently incubated in a humidified incubator at 37° C. Colonies were counted on the 14th day and converted into cfu/well. The results are represented at FIG. 1. From FIG. 1, it may be inferred that compounds of the present invention produces dose dependent reduction in mycobacterial cfu's in MYC 431 infected macrophages.

EXAMPLE 5

Figure 2:
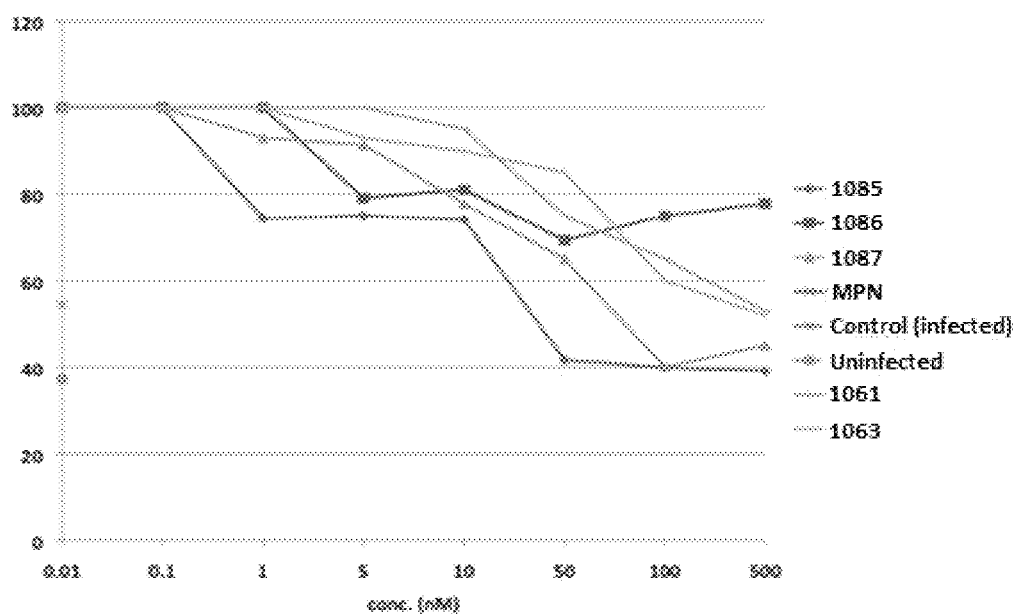
FIG. 2, depicts the effects of the compounds of the present invention on Lipid Bodies

Determination of the Effect of the Compounds of the Present Invention on Lipid Bodies THP-1 cells were seeded onto #1 thickness, 12 mm diameter glass cover-slips in 24-well tissue culture plates at a density of 0.3×106 cells per cover slip. These cells were then infected M. tb (H37Rv) at a MOI of 10 and incubated for 4 h at 370 C in 5% CO2. Extracellular bacteria were removed by washing and subsequently by supplementing the medium with 200 µg/ml amikacin for 2 h. SPR113 was added in increasing concentrations immediately after the amikacin treatment, and the medium containing the appropriate inhibitor was replenished at 16 h and 40 h post infection. At 48 hrs post infection cells were fixed with 3.7% para-formaldehyde and washed with PBS. HCS LipidTox Red neutral lipid stain, diluted 1:1000 in PBS was added to the cells for 30 min. The cell nuclei were stained using 300 nM DAPI solution (in H2O) for 5 min and then washed. Stained cells were observed with a Nikon EclipseTi-E laser scanning confocal microscope equipped with 60×/1.4NA Plan Apochromat DIC objective lens. DAPI and Lipid Tox were excited at 408 nm and 543 nm with a blue diode and a Helium-Neon laser respectively. The emissions were recorded through emission filters set at 450 and 605/75 nm. Images were acquired with a scanning mode format of 512×512 pixels. The transmission and detector gains were set to achieve best signal to noise ratios and the laser powers were tuned to limit bleaching fluorescence. All images were quantified using Image-Pro Plus version 6.0, a commercially available software package from Media Cybernetics. The results are represented herebelow at FIG. 2. FIG. 2 shows dose dependent reduction in cellular lipid bodies in the presence of the compounds of the present invention.

EXAMPLE 6

Effect of Compounds Against Different Mycobacterial Strains

Figure 3:
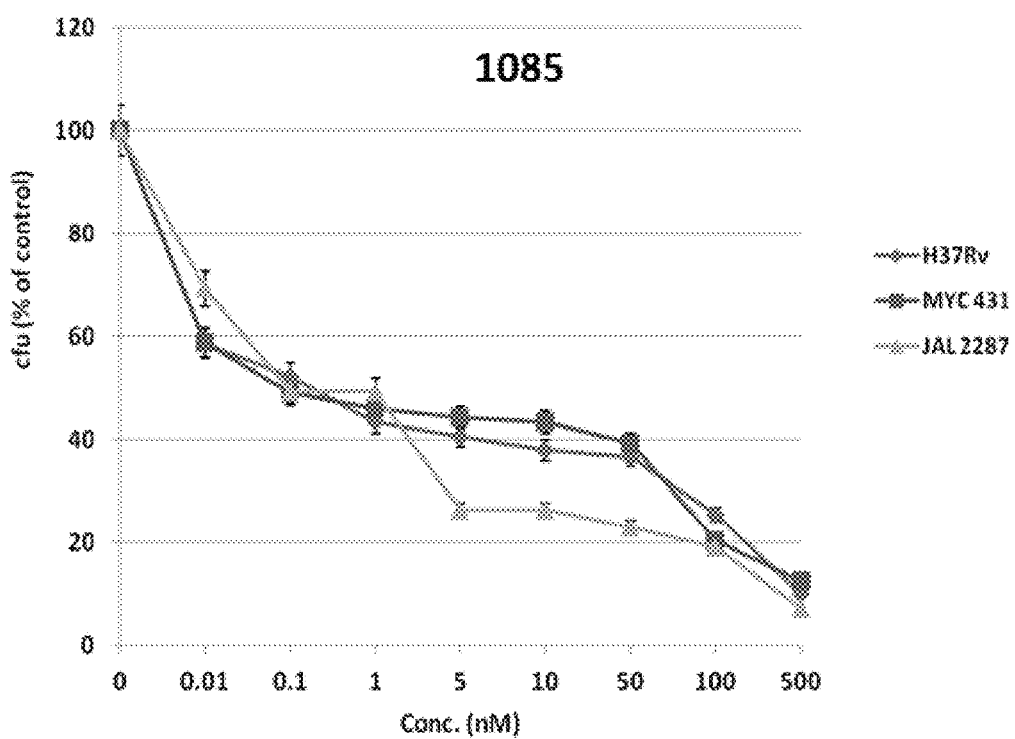
FIG. 3 depicts the potency of compound 1085 of the present invention in Cellular M. tb

THP-1 cells independently infected with r M. tb strains [JAL2287, JAL2261, XDR]. Addition of the media containing compound was performed at 16 hr and the medium containing the appropriate dose of compound was refreshed every 24 hr up to the 64 hr time point. At the end of the total culture period of 90 hr, cells were lysed and CFUs were determined and results are as shown graphically in FIG. 3. The cellular Potency of compound 1085 was measured in MTB infected THP1 and EC50 of H37Rv was 0.5 nM and MYC431 and JAL2287 were 0.1 nM. The graph shows that compound inhibited all the mycobacterial strains at concentration of 0.01 to 500 nM.

EXAMPLE 7

Effect of Compounds on c-AMP Levels

Figure 4:
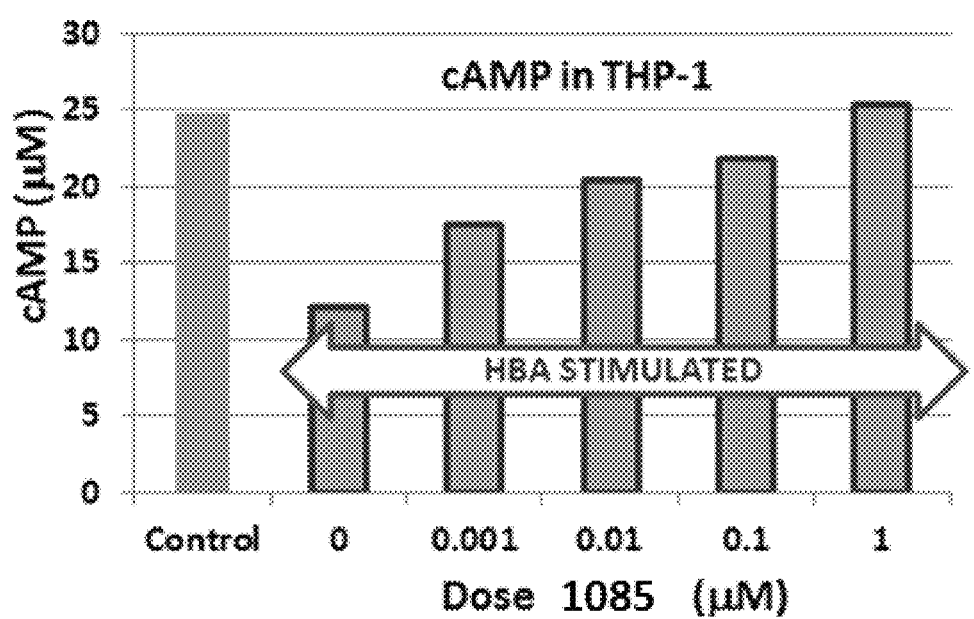
FIG. 4, represents the effect of compound 1085 on adenylyl cyclase (c-AMP) in THP-1 macrophages

THP-1 macrophages were incubated with compd. 1085 at the indicated concentrations for 30 min, following which 3-hydroxybutyric acid. (3HBA, 10 uM), a GPR109A agonist, was added to cells for 90 min. In the absence of compound 1085, 3HBA reduces intracellular cAMP levels while compound 1085 inhibits the activity in a dose dependent manner. The results are represented at FIG. 4.

EXAMPLE 8

Co-localization of M. tuberculosis with Degradative Vesicles: Acidified Lysosomes and Autophagosomes in the Presence of Compound 1085

Figure 5A:
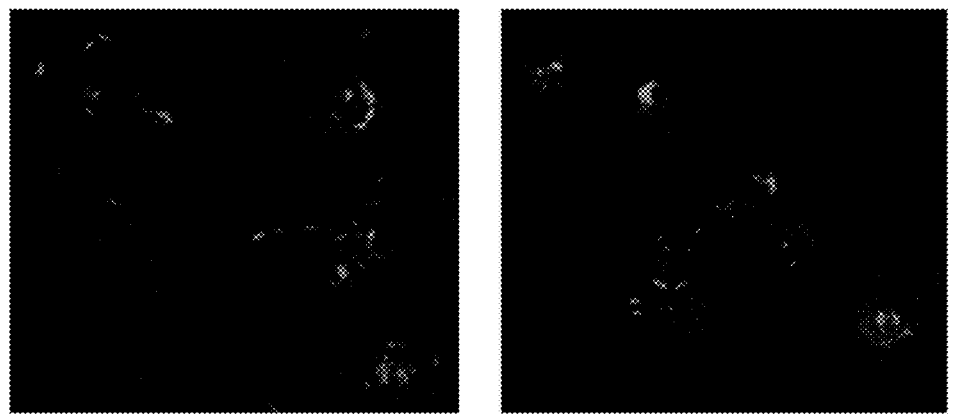
FIGS. 5a and 5b, represents the Co-localization of *M. tuberculosis* with degradative vesicles: acidified lysosomes and autophagosomes in the presence of compound 1085
Figure 5B:
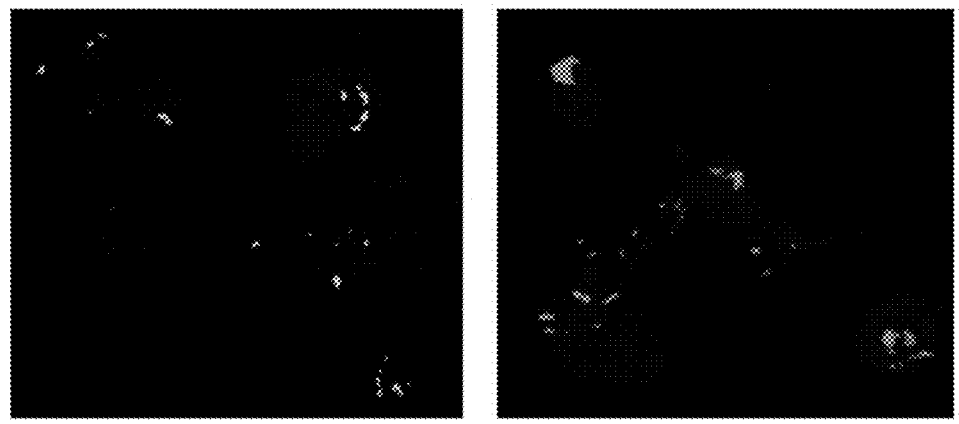

THP-1 cells were seeded onto glass cover-slips in 24-well tissue culture plates at a density of $0.3 \times 10^6$ cells per cover slip. These cells were then infected GFP-tagged M. tb (H37Rv-GFP) at a MOI of 10 and incubated for 4 h at 37° C. in 5% $CO_2$. Extracellular bacteria were removed by washing and subsequently by supplementing the medium with 200 µg/ml Amikacin for 2 hr. compound 1085 was added at 100 nM concentration immediately after the amikacin treatment, and the medium containing the compound was replenished at 16 h and 40 h post infection. At 48 h cells were incubated with 100 nM of the acidotropic dye for 60 min followed by fixation of cells with 3.7% para-formaldehyde for 20 min, and washed. The dye stained cells were permeabilized with 0.2% (v/v) Triton X-100 for 20 min, washed with PBS and blocking buffer 3% (w/v) BSA was added for 60 min. The cells were washed and LC3B rabbit Ab (Cell Signaling Technology), at a 1:200 dilution, was added for 60 min at room temperature. Cells were washed with PBST (once) and PBS (twice). Alexa Fluor 405 goat anti-rabbit Ab at 1:200 dilution was added for 45 min at room temperature. Cells were washed with PBST (once) and PBS (twice). The coverslips were mounted on slides with an antifade reagent. Stained cells were observed with a laser scanning confocal microscope. GFP and dyes were excited at 488 nm, 408 nm and 543 nm with an argon ion, blue diode and a Helium-Neon laser respectively. The emissions were recorded through emission filters set at 515/30; 450 and 605/75 nm. Serial confocal sections (0.5 m thick) within a z-stack spanning a total thickness of 10 m were taken in individual channels green, blue and red using the motor drive focusing system. Images were acquired with a scanning mode format of 512×512 pixels. The transmission and detector gains were set to achieve best signal to noise ratios and the laser powers were tuned to limit bleaching fluorescence. All images were quantified. The merged confocal images were deconvolved and subjected to co-localization analysis to determine the "Overlap Coefficient" as previously described (Manders et al, 1993). The results are presented at FIGS. 5a and 5b. Autophagosomes and acidified lysosomes are degradative vesicles that function in maintaining cellular homeostasis and are also an important component of the antimicrobial responses mounted by a macrophage to clear off intracellular infection. M. Tuberculosis modulates both these degradative pathways in order to ensure its continued survival within the macrophage. Interventions which lead to activation of these pathways in infected macrophages will lead to targeted killing of intracellular M. Tuberculosis and thus reduce mycobacterial load. The significance of the experiments done with compound 1085 is that treatment of infected macrophages with this compound leads to an increased co localization of mycobacteria with these degradative vesicles which is reflected by the increased value of the co localization coefficient (higher value of co localization coefficient indicates a higher percentage of bacteria present inside these degradative vesicles). The bacteria present inside these vesicles upon compound 1085 treatment are thus primed to be subsequently killed which in turn is reflected in the lower in vitro cfu's obtained with compound 1085.

EXAMPLE 9

GPR109A Specific Effect of Compound No. 1085 on Cellular Lipid Bodies

Figure 6:
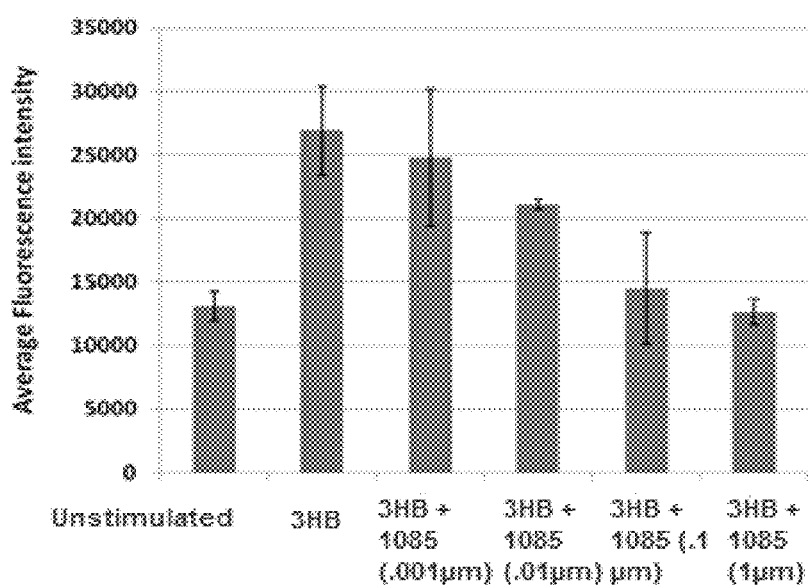
FIG. 6, represents the effect of compound 1085 on cellular lipid body

THP-1 cells were seeded onto glass cover-slips in 24-well tissue culture plates at a density of $0.3 \times 10^6$ cells per cover slip. Ligand for GPR109A, 3-HB (10 µM) was added to the cells and in parallel sets. Compd. 1085 was added in increasing concentrations. At 48 h post 3HB addition cells were fixed with 3.7% para-formaldehyde and washed with PBS. HCS LipidTox Red neutral lipid stain, diluted 1:1000 in PBS was added to the cells for 30 min. The cell nuclei were stained using 300 nM DAPI solution (in $H_2O$) for 5 min and then washed. Stained cells were observed with a laser scanning confocal microscope equipped with Apochromat DIC objective lens. DAPI and Lipid Tox were excited at 408 nm and 543 nm with a blue diode and a Helium-Neon laser respectively. The emissions were recorded through emission filters set at 450 and 605/75 nm. Images were acquired with a scanning mode format of 512×512 pixels. The transmission and detector gains were set to achieve best signal to noise ratios and the laser powers were tuned to limit bleaching fluorescence. All images were quantified and the results are graphically depicted in FIG. 6 which demonstrates that significant effect on average fluorescent intensity was observed in presence of compound 1085 representing decrease in the cellular lipid body.

EXAMPLE 10

Effect of Compound 1085 on Intracellular Mycobacterial Load in THP-1 Macrophages Infected Individually with 8 Different Strains of *M. tuberculosis*

The human monocyte/macrophage cell line THP-1 was cultured in RPMI 1640 supplemented with 10% FCS and were maintained between 2 and $10 \times 10^5$ cells per ml at 37° C. in a humidified, 5% $CO_2$ atmosphere. Before infection, cells were plated in 96 well plates at $1 \times 10^4$ cells per well and differentiated with PMA (30 ng/ml) for a period of 48 hrs. Bacteria were grown in Middlebrooke 7H9 broth supplemented with 10% ADC (Becton Dickinson), 0.4% Glycerol and 0.05% Tween 80 until the mid-log phase. The bacteria were then harvested, washed with RPMI and re-suspended in the same media. The suspension was dispersed by aspiration twelve times each with a 23- and then a 26-gauge needle, followed by an additional dispersion for 3 times through a 30-gauge needle. This suspension was allowed to stand for 5 min. The upper half of the suspension was then used for the experiments. Bacteria were quantified by measuring the absorbance at a wavelength 600 nm (0.6 O.D. corresponds to $\sim 100 \times 10^6$ bacteria).

Figure 7:
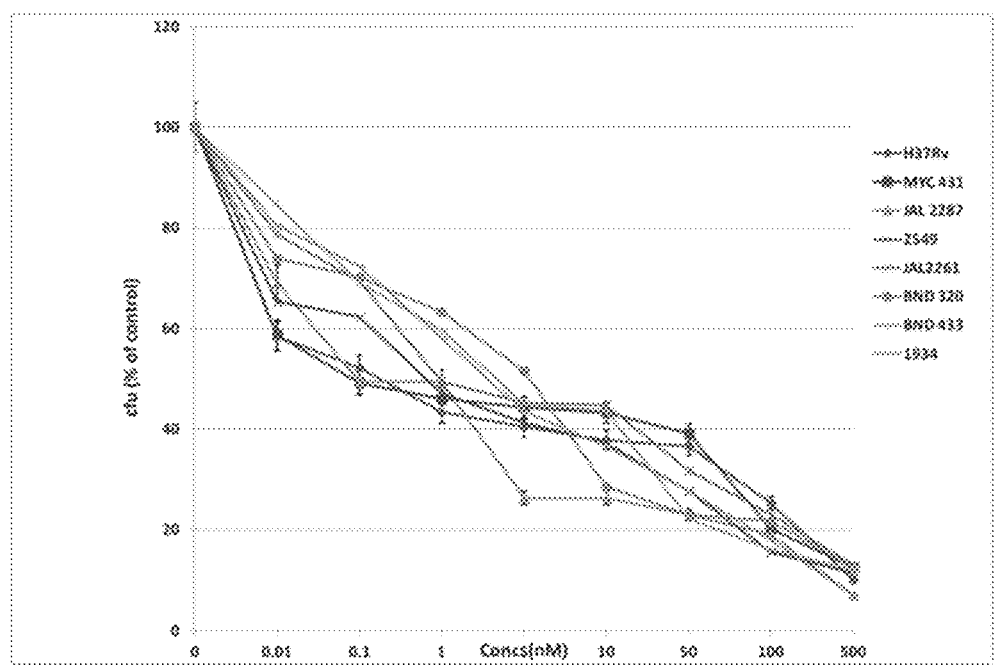
FIG. 7, represents the effect of compound 1085 on various mycobacterial strains

PMA-differentiated THP-1 cells were infected with tuberculosis bacteria at a MOI of 10 (i.e., 10 bacteria per cell). Infection was performed in antibiotic free RPMI supplemented with 10% FCS. After adding bacteria, culture plates were centrifuged at 700 rpm for 5 min prior to incubation at 37° C. with 5% $CO_2$. After 4 h, infected cells were washed twice with warm RPMI and replenished with complete RPMI containing 200 µg/mL amikacin for 2 h to remove any remaining extra-cellular bacteria. Subsequently, cells were washed and then maintained in complete RPMI for the rest of the experiment. Inhibitor addition was performed at 16 hrs post infection (p.i) and the medium containing the appropriate dose of inhibitor was replenished at 40 hrs and 64 hrs p.i. At 90 hr post infection, the cells were lysed in 50 µl of 0.06% SDS for 10 min at room temperature. Lysate dilutions of 1:10 were plated in duplicate sets on 7H11 agar plates. Square plates (12×12 cm) were used for the plating, by the track dilution method in which 10 µl of each dilution was spotted on one side of square plate. The plate was then tipped onto its side (at a 45°-90° angle), and the spots were allowed to gently flow in parallel tracks along the agar surface. The plates were then allowed to dry and subsequently incubated in a humidified incubator at 37° C. Colonies were counted on the 14th day and converted into cfu/well. The results are graphically depicted in FIG. 7 representing steady decrease in mycobacterial load with increase in concentration of compound 1085 for all 8 strains of *M. tuberculosis*.

EXAMPLE 11

Effect of Combinations of Compound 1085 with Known Anti-Mycobacterial Antibiotics on Intracellular Mycobacterial Load in THP-1 Macrophages Infected with *M. tuberculosis* H37Rv The human monocyte/macrophage cell line THP-1 was cultured in RPMI 1640 (Gibco Laboratories) supplemented with 10% FCS (Hyclone) and were maintained between 2 and $10 \times 10^5$ cells per ml at 37° C. in a humidified, 5% $CO_2$ atmosphere. Before infection, cells were plated in 96 well plates at $1 \times 10^4$ cells per well and differentiated with PMA (30 ng/ml) for a period of 48 hrs. Bacteria were grown in Middlebrooke 7H9 broth (Difco) supplemented with 10% ADC (Becton Dickinson), 0.4% Glycerol and 0.05% Tween 80 until the mid-log phase. The bacteria were then harvested, washed with RPMI and resuspended in the same media. The suspension was dispersed by aspiration twelve times each with a 23- and then a 26-gauge needle, followed by an additional dispersion for 3 times through a 30-gauge needle. This suspension was allowed to stand for 5 min. The upper half of the suspension was then used for the experiments. Bacteria were quantified by measuring the absorbance at a wavelength 600 nm (0.6 O.D. corresponds to $\sim 100 \times 10^6$ bacteria).

Figure 8:
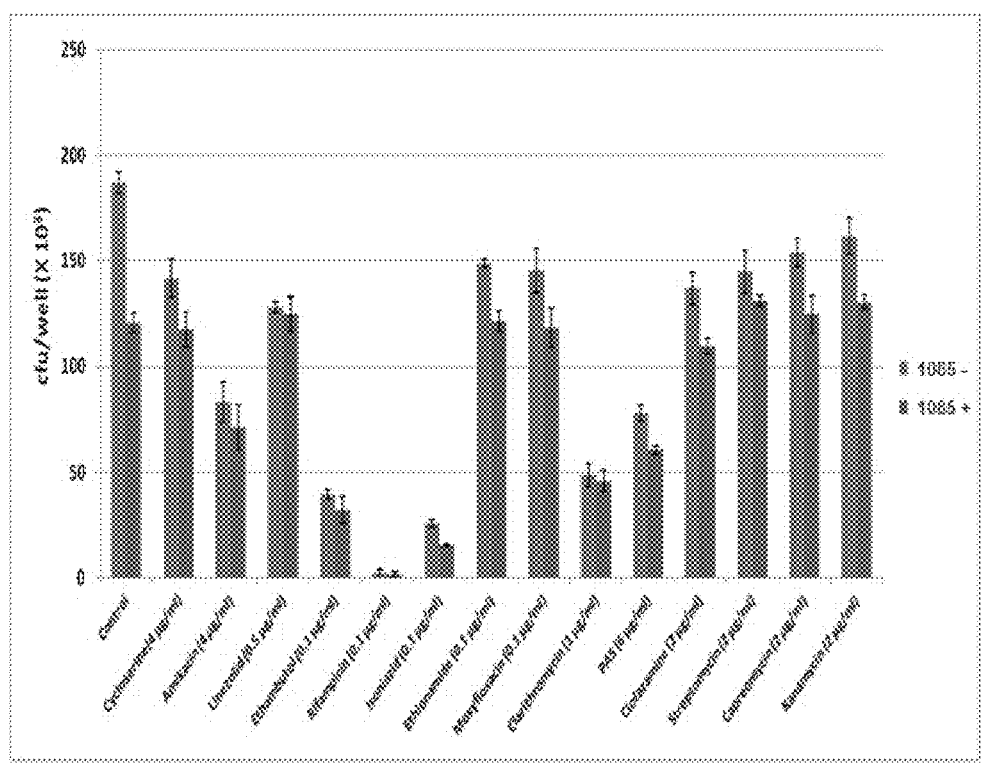
FIG. 8, represents the effect of compound 1085 on the mycobacterial growth alone and in combination with other pharmaceutical agents

PMA-differentiated THP-1 cells were infected with tuberculosis bacteria at a MOI of 10 (i.e., 10 bacteria per cell). Infection was performed in antibiotic free RPMI supplemented with 10% FCS. After adding bacteria, culture plates were centrifuged at 700 rpm for 5 min prior to incubation at 37° C. with 5% $CO_2$. After 4 h, infected cells were washed twice with warm RPMI and replenished with complete RPMI containing 200 µg/mL amikacin for 2 h to remove any remaining extra-cellular bacteria. Subsequently, cells were washed and then maintained in complete RPMI for the rest of the experiment. Inhibitor addition was performed at 16 hrs post infection (p.i) and the medium containing the appropriate dose of inhibitor was replenished at 40 hrs and 64 hrs p.i. At 90 h post infection, the cells were lysed in 50 µl of 0.06% SDS for 10 min at room temperature. Lysate dilutions of 1:10 were plated in duplicate sets on 7H11 agar plates. Square plates (12×12 cm) were used for the plating, by the track dilution method in which 10 µl of each dilution was spotted on one side of square plate. The plate was then tipped onto its side (at a 45°-90° angle), and the spots were allowed to gently flow in parallel tracks along the agar surface. The plates were then allowed to dry and subsequently incubated in a humidified incubator at 37° C. Colonies were counted on the 14th day and converted into cfu/well. The FIG. 8 shows that the compound 1085 does not negatively affect the activities of the known anti TB antibiotics and in some cases there might be additive/synergistic effects.

EXAMPLE 12

Compound 1085 Treatment in Mice (Oral Dosing)

Figure 9A:
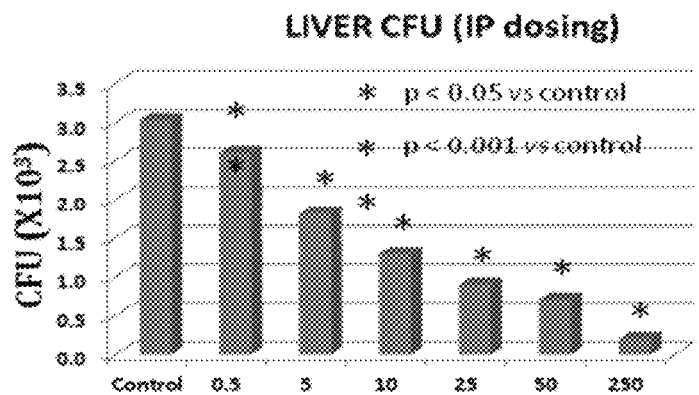
FIGS. 9a and 9b, represents the pharmacokinetic parameters of compound 1085 administered via intraperitoneal route
Figure 9B:
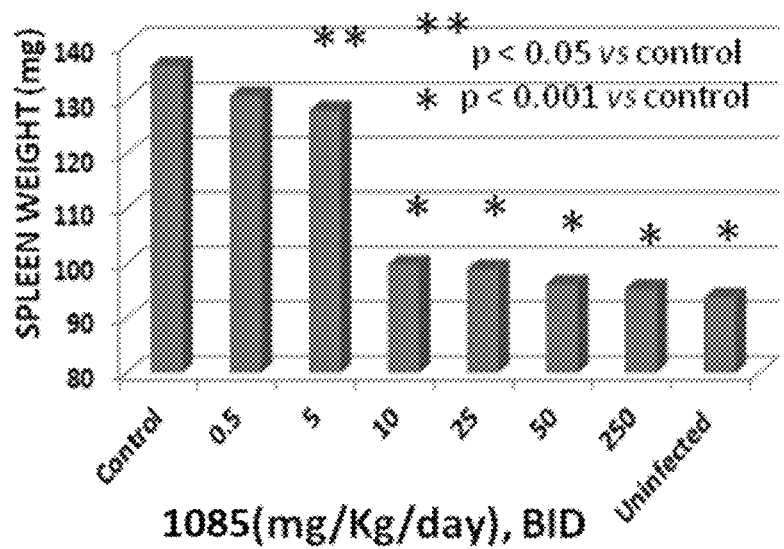

Groups of naive mice (female BALB/c mice 4-6 wk of age at 5/group) were infected with MDR-M. tb (JAL2287)

through the aerosol route by delivering between 150-200 bacteria per lung during 30 min of exposure. One group of mice was sacrificed 24 h later and lung homogenates were plated onto 7H11 agar plates for confirming infection. At fifteen days post infection, compound 1085 treatment was initiated by delivering the compound orally. Individual groups of mice were treated at the following doses: 100, 30, and 10 mg/kg body weight/day (1085 was solubilized in PEG400). At fourteen days following treatment, mice were sacrificed and lung and spleen enriched using a homogenizer. An aliquot (100 µl) of the serially diluted homogenate (10-2 & 10-3) was plated onto 7H11 agar plates for determining the mycobacterial load. The cfu's were counted at 18 days post plating on the agar plates. The results of pharmacokinetic parameters via intraperitoneal route are represented graphically at FIGS. 9a and 9b. The pharmacokinetic parameter via oral route is presented herebelow at Table 3 and 4. From the figures and tables it may be inferred that compounds of the present invention, illustrated by an exemplary compound 1085 were found to be effective at all experimental doses. The pharmacokinetic (PK) data of compound 1085 is represented in Table 5 and 6 demonstrating that compound 1085 has very good bioavailability in both mouse and dog.

TABLE 3

Reduction of CFU in lung (Oral Dosing)

| Compd. 1085 (mg/kg/day) | CFU/Lung (×10$^5$) | % Reduction | p value |
|---|---|---|---|
| 0 | 38.6 | | |
| 10 | 21.8 | 43.5 | 0.0001 |
| 30 | 14.5 | 62.4 | 0.0001 |
| 100 | 7.8 | 80.0 | 0.0001 |

TABLE 4

Reduction of CFU in spleen (Oral Dosing)

| Compd. 1085 (mg/kg/day) | CFU/spleen (×10$^3$) | % Reduction | p value |
|---|---|---|---|
| 0 | 11.8 | | |
| 10 | 0.4 | 96.6 | 0.0001 |
| 30 | 0.2 | 98.3 | 0.0001 |
| 100 | 0.2 | 98.3 | 0.0001 |

TABLE 5

PK data of Compound 1085 in Mouse
PK DATA (Balb/C mouse)

| Parameters | 10 mpk, PO | 1 mpk, IV |
|---|---|---|
| Cmax (nM) | 11163 | 3057 |
| Tmax (h) | 0.2 | 0 |
| AUC (nM * h) | 8170 | 1728 |
| T½ (h) | 2.8 | 1.9 |
| Cl (L/Kg/h) | 0.12 | 0.08 |
| Vd (L/Kg) | 0.13 | 0.22 |

Mouse bioavailability: 47%

TABLE 6

PK data of Compound 1085 in Dog
PK DATA (Beagle dog)

| Parameters | 3 mpk, PO | 0.3 mpk, IV |
|---|---|---|
| Cmax (nM) | 3775 | 2756 |
| Tmax (h) | 1.0 | 0 |
| AUC 0-24 (nM * h) | 19555 | 3437 |
| T½ (h) | 2.5 | 3.0 |
| Cl (L/Kg/h) | — | — |
| Vd (L/Kg) | — | — |

Dog Bioavailability: 57%

EXAMPLE 13

Compound 1085+ATT Combination Treatment in Mice (Oral Dosing)

Figure 10:
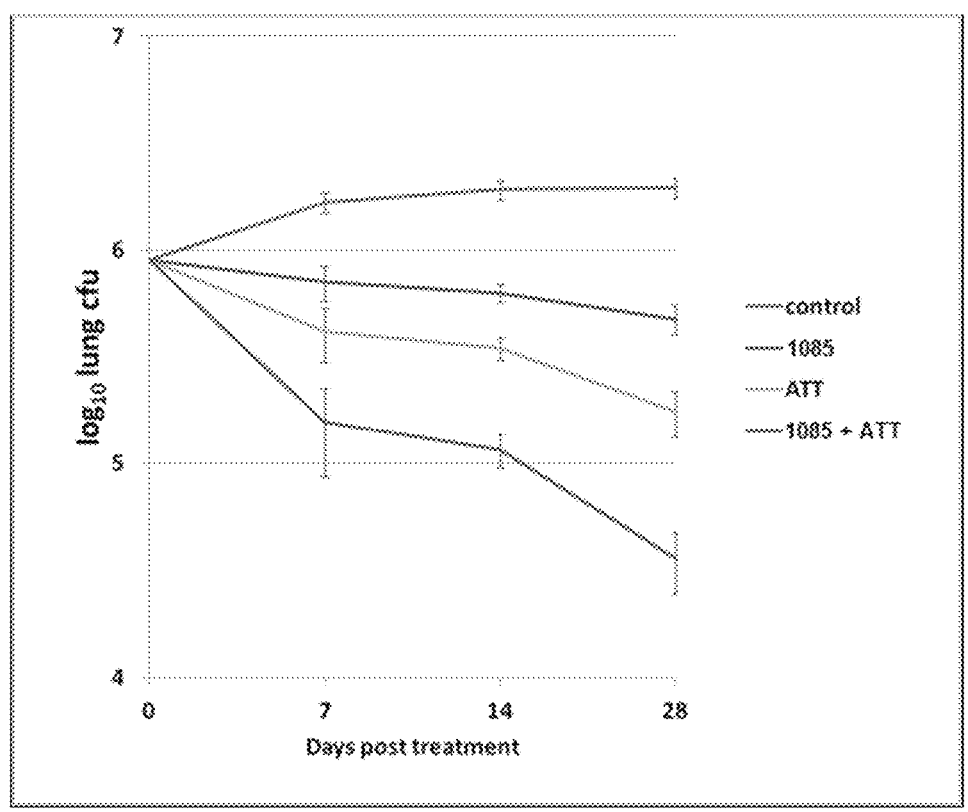
FIG. 10, represents the combination treatment of compound 1085 with Antituberculer therapy (ATT)

Groups of naive mice (female BALB/c mice 4-6 wk of age at 5/group) were infected with drug susceptible M. tb (H37Rv) through the aerosol route by delivering between 150-200 bacteria per lung during 30 min of exposure. One group of mice was sacrificed 24 h later and lung homogenates were plated onto 7H11 agar plates for confirming infection. At fifteen days post infection, oral drug treatment was initiated with a single dose per day. One group received Anti-TB therapy, ATT (Isoniazid: 1.5 mg/kg+Rifampicin: 1 mg/kg+Pyrazinamide: 1.5 mg/kg+Ethambutol: 1.5 mg/kg), one group received compd. 1085 (10 mg/kg) and a parallel group received a combination of comd. 1085 and ATT (Isoniazid: 1.5 mg/kg+Rifampicin: 1 mg/kg+Pyrazinamide: 1.5 mg/kg+Ethambutol: 1.5 mg/kg+Compound 1085: 10 mg/kg). At 1 week, 2 weeks and 4 weeks post treatment mice were sacrificed along with a control (mocka treated) group and lungs enriched using a homogenizer. An aliquot (100 µl) of the serially diluted homogenate ($10^{-2}$ & $10^{-3}$) was plated onto 7H11 agar plates for determining the mycobacterial load. The CFU's were counted at 18 days post plating on the agar plates. Combination treatment of compd. 1085 with ATT demonstrates significant reduction in lung CFU as depicted in FIG. 10. The data is represented in below Table 7.

TABLE 7

Combination treatment of compd. 1085 with ATT

| GROUP | CFU/Lung (×10$^5$) | SD |
|---|---|---|
| Untreated | 19.54 | 2.09 |
| Compd. 1085 (10 mg/kg) | 4.76 | 0.76 |
| ATT | 1.76 | 0.42 |
| Isoniazid: 1.5 mg/kg | | |
| Rifampicin: 1 mg/kg | | |
| Pyrazinamide: 1.5 mg/kg | | |
| Ethambutol: 1.5 mg/kg | | |
| Compd. 1085 + ATT | 0.36 | 0.11 |

The invention claimed is:

1. A method for treatment of an infection caused by resistant or non-resistant *Mycobacterium tuberculosis*, comprising administering to a subject in need thereof a compound of structural Formula (1), including its salts, hydrates or stereoisomers:

Formula 1

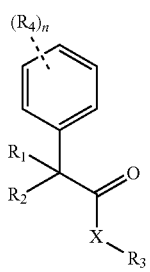

wherein
X is O, NH or N(alkyl);
R$_1$ and R$_2$ are independently hydrogen, but with the proviso that R$_1$ and R$_2$ are not both hydrogen, deuterium, hydroxyl, C$_{1-10}$ straight chain or branched chain alkyl, 3-7 membered cycloalkyl, C$_{1-6}$alkoxy, aryl, amino, NH(alkyl), N(alkyl)$_2$,OCOR$_5$, heteroaryl containing 1-3 heteroatoms selected from the group consisting of O, N and S; or R$_1$ and R$_2$ may combined to form an aryl or a heteroaryl ring containing 1-3 heteroatoms selected from the group consisting of O, N and S; R$_3$ is a non-aromatic heterocyclic ring or fused heterocyclic ring selected from:

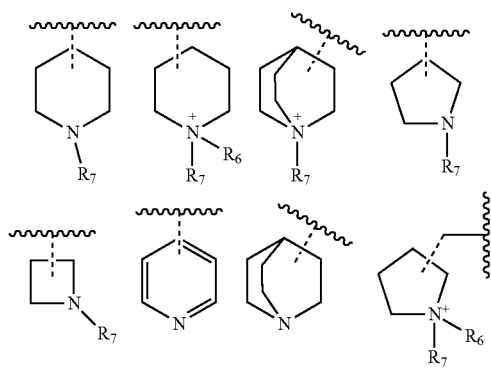

X may in conjunction with R$_3$ form a 5-7 membered heterocyclic ring comprising 1-3 heteroatoms selected from group consisting of N, O and S, wherein the heterocyclic ring be further substituted with one or more lower alkyl groups, halogens, amino, NH(alkyl), N(alkyl)$_2$, NH-aralkyl;
R$_4$ is a hydrogen, lower straight chain or branched alkyl, halogen, deuterium, C$_{1-6}$alkoxy, amino, NH(alkyl), N(alkyl)$_2$, —COOR$_8$, or CONR$_8$R$_9$;
R$_5$ is hydrogen, hydroxy, C$_{1-6}$alkyl, C$_{1-6}$alkoxy, amino, NH(alkyl), or N(alkyl)$_2$;
R$_6$ and R$_7$ are independently selected from the group consisting of hydrogen, C$_{1-10}$alkyl, —COR$_8$, —CH$_2$OCOR$_8$, —CH$_2$OCONHR$_8$R$_9$, —COOR$_8$, —CONR$_8$R$_9$, —SO$_2$R$_8$, aryl, and aralkyl;
R$_8$ and R$_9$ are independently selected from the group consisting of hydrogen, and C$_{1-6}$ straight chain or branched chain alkyl; and
n is 1, 2, or 3.

2. The method of claim 1, wherein the infection is drug-sensitive, mono-drug resistance, multi drug-resistant (MDR), extensively drug-resistant (XDR) or totally drug resistant (TDR) tuberculosis caused by a strain of *Mycobacterium tuberculosis*.

3. The method of claim 1, wherein in the compound of structural Formula (1):
X is NH;
R$_1$ and R$_2$ are independently selected from hydrogen, hydroxyl, C$_{1-10}$ alkyl,C$_{1-6}$alkox;
R$_3$ is selected from substituted aromatic or non-aromatic heterocyclic ring or fused heterocyclic ring selected from:

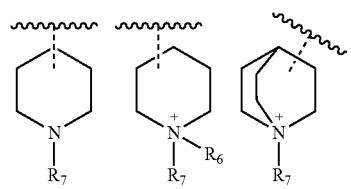

R$_4$ is selected from hydrogen, deuterium, halogen, C$_{1-6}$ straight chain or branched chain alkyl,
C$_{1-6}$ alkoxy, amino, NH(alkyl), N(alkyl)$_2$;
R$_6$ and R$_7$ are independently selected from hydrogen, C$_{1-10}$ alkyl, —COR$_8$, —CH$_2$OCOR$_8$, —CH$_2$OCONHR$_8$R$_9$, —COOR$_8$, —CONR$_8$R$_9$, —SO$_2$R$_8$, phenyl, benzyl;
R$_8$ and R$_9$ are independently selected from hydrogen or C$_{1-6}$ straight chain or branched chain alkyl; and
n is 1,2 or 3.

4. The method of claim 1, wherein the compound of Formula (1), including its salts, hydrates and stereoisomers thereof wherein said compound is selected from the group consisting of:
i. 1-Methylpiperidin-3-yl-2-hydroxy-2,2-diphenylacetate;
ii. 3-(2-Hydroxy-2,2-diphenylacetoxy)-1-(((isopropylcarbamoyl)oxy)methyl)-1-methylpiperidin-1-ium;
iii. Piperidin-3-yl 2-hydroxy-2,2-diphenylacetate;
iv. 1-Benzylpiperidin-3-yl 2-hydroxy-2,2-diphenylacetate;
v. 1-(Methylsulfonyl)piperidin-3-yl 2-hydroxy-2,2-diphenylacetate;
vi. 1-(Dimethylcarbamoyl) piperidin-3-yl 2-hydroxy-2,2-diphenylacetate;
vii. 1-Benzylpiperidin-4-yl 2-hydroxy-2,2-diphenylacetate;
viii. 3-(2-Hydroxy-2,2-diphenylacetoxy)-1-methylquinuclidin-1-ium;
ix. 1-Benzylpyrrolidin-3-yl 2-hydroxy-2,2-diphenylacetate;
x. 1-Ethylpiperidin-3-yl 2-hydroxy-2,2-diphenylacetate;
xi. 1-(Isopropylcarbamoyl) piperidin-3-yl 2-hydroxy-2,2-diphenylacetate;
xii. 1-Propylpiperidin-3-yl 2-hydroxy-2,2-diphenylacetate;
xiii. 1-Methylpiperidin-4-yl 2-hydroxy-2,2-diphenylacetate;
xiv. 1-Benzylazetidin-3-yl 2-hydroxy-2,2-diphenylacetate;
xv. 1-Acetylpiperidin-3-yl 2-hydroxy-2,2-diphenylacetate;
xvi. 2-Hydroxy-2,2-diphenyl-N-(piperidin-3-yl)acetamide;
xvii. N-(1-Benzylpiperidin-4-yl)-2-hydroxy-2,2-diphenylacetamide;
xviii. 1-Methylpyrrolidin-3-yl 2-hydroxy-2,2-diphenylacetate;

xix. Quinuclidin-3-yl 2-hydroxy-2,2-diphenylacetate;
xx. 2-Hydroxy-N-(1-methylpiperidin-3-yl)-2,2-diphenylacetamide;
xxi. N-(1-Benzylpiperidin-4-yl)-2-hydroxy-2,2-diphenylacetamide;
xxii. N-(1-Benzylazetidin-3-yl)-2-hydroxy-2,2-diphenylacetamide;
xxiii. Azetidin-3-yl 2-hydroxy-2,2-diphenylacetate;
xiv. (S)-1-Benzylpiperidin-3-yl 2-hydroxy-2,2-diphenylacetate;
xv. (R)-1-Benzylpiperidin-3-yl 2-hydroxy-2,2-diphenylacetate;
xvi. (S)-1-Methylpiperidin-3-yl 2-hydroxy-2,2-diphenylacetate;
xvii. (R)-1-Methylpiperidin-3-yl 2-hydroxy-2,2-diphenylacetate;
xviii. (R)-N-(1-Benzylpiperidin-3-yl)-2-hydroxy-2,2-diphenylacetamide;
xxix. (R)-N-(1-Benzylpiperidin-3-yl)-2-hydroxy-2,2-diphenylacetamide;
xxx. 2-Hydroxy-2,2-diphenyl-N-(piperidin-4-yl)acetamide;
xxxi. (S)-2-Hydroxy-N-(1-methylpiperidin-3-yl)-2,2-diphenylacetamide;
xxxii. (R)-2-Hydroxy-N-(1-methylpiperidin-3-yl)-2,2-diphenylacetamide;
xxxiii. 1-Benzylazetidin-3-yl 2-hydroxy-2-phenylpropanoate;
xxxiv. (R)-N-(1-Benzylpiperidin-3-yl)-2,2-diphenylacetamide;
xxxv. N-((S)-1-Benzylpiperidin-3-yl)-2-hydroxy-2-phenylacetamide;
xxxvi. N-((R)-1-Benzylpiperidin-3-yl)-2-hydroxy-2-phenylpropanamide;
xxxvii. (R)-(R)-1-Methylpiperidin-3-yl 2-hydroxy-2-phenylacetate;
xxxviii. (R)-(S)-1-Methylpiperidin-3-yl 2-hydroxy-2-phenylacetate;
xxxix. (S)-(R)-1-Methylpiperidin-3-yl 2-hydroxy-2-phenylacetate;
xl. (S)-(S)-1-Methylpiperidin-3-yl 2-hydroxy-2-phenylacetate;
xli. (R)-1-Methylpiperidin-4-yl 2-hydroxy-2-phenylacetate;
xlii. (S)-2-Hydroxy-N-(1-methylpiperidin-4-yl)-2-phenylacetamide;
xliii. (R)-2-Hydroxy-N-(1-methylpiperidin-4-yl)-2-phenylacetamide;
xliv. (R)-2-Hydroxy-N-((R)-1-methylpiperidin-3-yl)-2-phenylacetamide;
xlv. (R)-2-Hydroxy-N-((S)-1-methylpiperidin-3-yl)-2-phenylacetamide;
xlvi. (S)-2-Hydroxy-2-phenyl-N-(pyridin-3-yl)acetamide;
xlvii. (S)-1-Methylpiperidin-4-yl 2-hydroxy-2-phenylacetate;
xlviii. (S)-1-Benzylazetidin-3-yl 2-hydroxy-2-phenylacetate;
xlix. (S)-(R)-Quinuclidin-3-yl 2-hydroxy-2-phenylacetate;
l. (S)-(S)-Quinuclidin-3-yl 2-hydroxy-2-phenylacetate;
li. (R)-N-(1-Benzylpiperidin-4-yl)-2-hydroxy-2-phenylacetamide;
lii. (S)-N-(1-Benzylpiperidin-4-yl)-2-hydroxy-2-phenylacetamide;
liii. (R)-3-((R)-2-Hydroxy-2-phenylacetoxy)-1,1-dimethylpiperidin-1-ium;
liv. (S)-3-((R)-2-Hydroxy-2-phenylacetoxy)-1,1-dimethylpiperidin-1-ium;
lv. (R)-2-Hydroxy-2-phenyl-N-(pyridin-3-yl)acetamide;
lvi. (R)-(S)-1-Methylpiperidin-3-yl 2-acetoxy-2-phenylacetate;
lvii. (R)-(R)-1-Methylpyrrolidin-3-yl 2-hydroxy-2-phenylacetate;
lviii. (R)-(S)-1-Methylpyrrolidin-3-yl 2-hydroxy-2-phenylacetate;
lix. (S)-(R)-1-Methylpiperidin-3-yl 2-methoxy-2-phenylacetate;
lx. (R)-2-Hydroxy-2-phenyl-N-(piperidin-4-yl)acetamide;
lxi. (R)-Piperidin-4-yl 2-hydroxy-2-phenylacetate;
lxii. (R)-3-(2-Hydroxy-2,2-diphenylacetoxy)-1,1-dimethylpiperidin-1-ium;
lxiii. (R)-3-(2-Hydroxy-2,2-diphenylacetoxy)-1,1-dimethylpiperidin-1-ium;
lxiv. (R)-3-((R)-2-Hydroxy-2-phenylacetoxy)-1,1-dimethylpiperidin-1-ium;
lxv. (R)-3-((R)-2-Hydroxy-2-phenylacetoxy)-1,1-dimethylpiperidin-1-ium;
lxvi. (S)-(R)-1-Methylpiperidin-3-yl 2-methoxy-2-phenylacetate;
lxvii. (S)-(S)-1-Methylpiperidin-3-yl 2-methoxy-2-phenylacetate;
lxviii. (S)-2-Hydroxy-N-((R)-1-methylpiperidin-3-yl)-2-phenylacetamide;
lxix. (S)-2-Hydroxy-N-((S)-1-methylpiperidin-3-yl)-2-phenylacetamide;
lxx. 3-(2,2-Diphenylacetamido)-1,1-dimethylpiperidin-1-ium;
lxxi. (2S)-1-Benzyl-2-((2,2-diphenylacetamido)methyl)-1-methylpyrrolidin-1-ium;
lxxii. 3-(2-Hydroxy-2,2-diphenylacetamido)-1,1-dimethylpiperidin-1-ium;
lxxiii. (R)-2-Methoxy-1-((S)-3-methylmorpholino)-2-phenylethanone;
lxxiv. (1S,3R)-1-Benzyl-3-(2,2-diphenylacetamido)-1-methylpiperidin-1-ium;
lxxv. (1S,3R)-1-Benzyl-3-(2,2-diphenylacetamido)-1-methylpiperidin-1-ium;
lxxvi. (1R,3R)-1-Benzyl-3-(2,2-diphenylacetamido)-1-methylpiperidin-1-ium;
lxxvii. 1-(3-(Benzylamino)piperidin-l-yl)-2,2-diphenylethanone;
lxxviii. N-((1-Benzylpyrrolidin-2-yl)methyl)-2,2-diphenylacetamide;
lxxix. 1-Benzyl-2-((2,2-diphenylacetamido)methyl)-1-methylpyrrolidin-1-ium;
lxxx. (R)-2-Methoxy-2-phenyl-N-(piperidin-4-yl)acetamide;
lxxxi. 2-Hydroxy-2-phenyl-N-(piperidin-4-yl)acetamide;
lxxxii. (S)-2-Hydroxy-2-phenyl-N-(piperidin-4-yl)acetamide;
lxxxiii. (S)-2-Methoxy-2-phenyl-N-(piperidin-4-yl)acetamide;
lxxxiv. 2-Hydroxy-2-phenyl-N-(piperidin-4-yl)propanamide;
lxxxv. 2-(3-Bromo-2,6-difluorophenyl)-2-hydroxy-N-(piperidin-4-yl)acetamide;
lxxxvi. (R)-2-Methoxy-N-methyl-2-phenyl-N-(piperidin-4-yl)acetamide;
lxxxvii. (R)-N-(1-Benzylpiperidin-4-yl)-2-methoxy-N-methyl-2-phenylacetamide;
lxxxviii. (S)-1-Benzylpiperidin-4-yl 2-methoxy-2-phenylacetate; and lxxxix. (R)-Ethyl 4-(2-methoxy-2-phenylacetamido)piperidine-1-carboxylate.

5. The method of claim 1, wherein the compound having Formula (1), including its salts, hydrates and stereoisomers thereof is selected from the group consisting of:
   i. (R)-2-Methoxy-2-phenyl-N-(piperidin-4-yl)acetamide;
   ii. 2-Hydroxy-2-phenyl-N-(piperidin-4-yl)acetamide;
   iii. (S)-2-Hydroxy-2-phenyl-N-(piperidin-4-yl)acetamide;
   iv. (S)-2-Methoxy-2-phenyl-N-(piperidin-4-yl)acetamide;
   v. 2-Hydroxy-2-phenyl-N-(piperidin-4-yl)propanamide;
   vi. 2-(3-Bromo-2,6-difluorophenyl)-2-hydroxy-N-(piperidin-4-yl)acetamide;
   vii. (R)-2-Hydroxy-2-phenyl-N-(piperidin-4-yl)acetamide; and
   viii. (R)-3-(2-Hydroxy-2,2-diphenylacetoxy)-1,1-dimethylpiperidin-1-ium.

6. A method for treatment of an infection caused by resistant or non-resistant *Mycobacterium tuberculosis*, comprising inhibiting GPR109A in the *Mycobacterium tuberculosis* by a compound of structural Formula (1), including its salts, hydrates or stereoisomers:

Formula 1 wherein
X is O, NH or N(alkyl);
$R_1$ and $R_2$ are independently hydrogen, but with the proviso that $R_1$ and $R_2$ are not both hydrogen, deuterium, hydroxyl, $C_{1-10}$ straight chain or branched chain alkyl, 3-7 membered cycloalkyl, $C_{1-6}$alkoxy, aryl, amino, NH(alkyl), N(alkyl)$_2$, OCOR$_5$, heteroaryl containing 1-3 heteroatoms selected from the group consisting of O, N and S; or $R_1$ and $R_2$ may combined to form an aryl or a heteroaryl ring containing 1-3 heteroatoms selected from the group consisting of O, N and S;
$R_3$ is a non-aromatic heterocyclic ring or fused heterocyclic ring selected from:

X may in conjunction with $R_3$ form a 5-7 membered heterocyclic ring comprising 1-3 heteroatoms selected from group consisting of N, O and S, wherein the heterocyclic ring be further substituted with one or more lower alkyl groups, halogens, amino, NH(alkyl), N(alkyl)$_2$, NH-aralkyl;
$R_4$ is a hydrogen, lower straight chain or branched alkyl, halogen, deuterium, $C_{1-6}$ alkoxy, amino, NH(alkyl), N(alkyl)$_2$, —COOR$_8$, or CONR$_8$R$_9$;
$R_5$ is hydrogen, hydroxy, $C_{1-6}$alkyl, $C_{1-6}$alkoxy, amino, NH(alkyl), or N(alkyl)$_2$;
$R_6$ and $R_7$ are independently selected from the group consisting of hydrogen, $C_{1-10}$ alkyl, —COR$_8$, —CH$_2$OCOR$_8$, —CH$_2$OCONHR$_8$R$_9$, —COOR$_8$, —CONR$_8$R$_9$, —SO$_2$R$_8$, aryl, and aralkyl;
$R_8$ and $R_9$ are independently selected from the group consisting of hydrogen, and $C_{1-6}$ straight chain or branched chain alkyl; and
n is 1, 2, or 3.

7. The method of claim 6, wherein the infection is drug-sensitive, mono-drug resistance, multi drug-resistant (MDR), extensively drug-resistant (XDR) or totally drug resistant (TDR) tuberculosis caused by a strain of *Mycobacterium tuberculosis*.

8. A method for treatment of resistant or non-resistant tuberculosis infection in a subject in need thereof, comprising inhibiting GPR109A in the subject by a compound of structural Formula (1), including its salts, hydrates or stereoisomers:

Formula 1 wherein
X is O, NH or N(alkyl);
$R_1$ and $R_2$ are independently hydrogen, but with the proviso that $R_1$ and $R_2$ are not both hydrogen, deuterium, hydroxyl, $C_{1-10}$ straight chain or branched chain alkyl, 3-7 membered cycloalkyl, $C_{1-6}$alkoxy, aryl, amino, NH(alkyl), N(alkyl)$_2$, OCOR$_5$, heteroaryl containing 1-3 heteroatoms selected from the group consisting of O, N and S; or $R_1$ and $R_2$ may combined to form an aryl or a heteroaryl ring containing 1-3 heteroatoms selected from the group consisting of O, N and S;
$R_3$ is a non-aromatic heterocyclic ring or fused heterocyclic ring selected from:

-continued

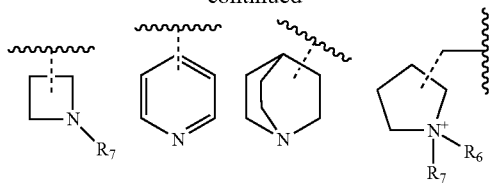

X may in conjunction with $R_3$ form a 5-7 membered heterocyclic ring comprising 1-3 heteroatoms selected from group consisting of N, O and S, wherein the heterocyclic ring be further substituted with one or more lower alkyl groups, halogens, amino, NH(alkyl), N(alkyl)$_2$, NH-aralkyl;

$R_4$ is a hydrogen, lower straight chain or branched alkyl, halogen, deuterium, $C_{1-6}$ alkoxy, amino, NH(alkyl), N(alkyl)$_2$, —COOR$_8$, or CONR$_8$R$_9$;

$R_5$ is hydrogen, hydroxy, $C_{1-6}$alkyl, $C_{1-6}$alkoxy, amino, NH(alkyl), or N(alkyl)$_2$;

$R_6$ and $R_7$ are independently selected from the group consisting of hydrogen, $C_{1-10}$ alkyl, —COR$_8$, —CH$_2$OCOR$_8$, —CH$_2$OCONHR$_8$R$_9$, —COOR$_8$, —CONR$_8$R$_9$, —SO$_2$R$_8$, aryl, and aralkyl;

$R_8$ and $R_9$ are independently selected from the group consisting of hydrogen, and $C_{1-6}$ straight chain or branched chain alkyl; and n is 1, 2, or 3.

9. The method of claim 8, wherein the infection is drug-sensitive, mono-drug resistance, multi drug-resistant (MDR), extensively drug-resistant (XDR) or totally drug resistant (TDR) tuberculosis caused by a strain of *Mycobacterium tuberculosis*.

* * * * *